US007734321B2

(12) United States Patent
White

(10) Patent No.: US 7,734,321 B2
(45) Date of Patent: Jun. 8, 2010

(54) APPARATUS FOR NON-INVASIVE SPECTROSCOPIC MEASUREMENT OF ANALYTES, AND METHOD OF USING THE SAME

(75) Inventor: Steve C. White, La Quinta, CA (US)

(73) Assignee: All Protect, LLC, La Quinta, CA (US)

( * ) Notice: Subject to any disclaimer, the term of this patent is extended or adjusted under 35 U.S.C. 154(b) by 146 days.

(21) Appl. No.: 11/945,992

(22) Filed: Nov. 27, 2007

(65) Prior Publication Data

US 2009/0018420 A1 Jan. 15, 2009

Related U.S. Application Data

(60) Provisional application No. 60/949,836, filed on Jul. 13, 2007, provisional application No. 60/966,028, filed on Aug. 24, 2007.

(51) Int. Cl.
*A61B 5/145* (2006.01)
(52) U.S. Cl. .................. 600/310; 600/340; 600/344
(58) Field of Classification Search .................. 600/310, 600/340, 344
See application file for complete search history.

(56) References Cited

U.S. PATENT DOCUMENTS

| | | | |
|---|---|---|---|
| 5,070,874 A * | 12/1991 | Barnes et al. ............... | 600/316 |
| 5,361,758 A | 11/1994 | Hall et al. | |
| 5,429,128 A | 7/1995 | Cadell et al. | |
| 5,515,847 A | 5/1996 | Braig et al. | |
| 5,743,349 A | 4/1998 | Steinberg | |

(Continued)

FOREIGN PATENT DOCUMENTS

WO WO 03/091711 A1 11/2003

OTHER PUBLICATIONS

Ghionea, Simon; "Ethanol Sensing for Detecting Blood Alcohol Concentration," ECE499 Paper, Winter 2006, 18 pgs.

(Continued)

*Primary Examiner*—Eric F Winakur
*Assistant Examiner*—Etsub D Berhanu
(74) *Attorney, Agent, or Firm*—Christie, Parker & Hale, LLP

(57) ABSTRACT

An apparatus for spectroscopic evaluation of a subject's body fluids may be used at the interstitial region adjacent to or in between a subject's extremities using a spectroscopic probe. The spectroscopic probe may possess one or more of the movements such as rotational, translational, and/or vertical freedom necessary for the probe to contact the subject's tissue at a consistent angle and pressure while accommodating the different size of the subject's extremities, and may be housed in a device optimized for attaining reproducible blood flow to the region of the subject that is measured, and for minimizing the effects of the housing pulling, stretching, pressing, compressing the subject's skin. A pressure sensor may be used to ensure that measurements are taken at an optimal pressure. A touch sensor may be used to activate a system and/or to ensure flushness. In addition, the spectroscopic measurement may be coupled with a temperature measurement means that detects the subject's local body temperature in or near the region being measured, or the subject's core or mean body temperature, or the ambient temperature proximate to the probe, or any combination of those measurements. The system may also include one or more indicators to communicate information to a test subject.

22 Claims, 31 Drawing Sheets

U.S. PATENT DOCUMENTS

| | | | |
|---|---|---|---|
| 5,755,226 A * | 5/1998 | Carim et al. | 600/323 |
| 5,810,724 A * | 9/1998 | Gronvall | 600/323 |
| 6,229,908 B1 | 5/2001 | Edmonds, III et al. | |
| 6,285,895 B1 * | 9/2001 | Ristolainen et al. | 600/323 |
| 6,626,537 B1 | 9/2003 | Odom et al. | |
| 6,914,668 B2 | 7/2005 | Brestel et al. | |
| 7,003,337 B2 | 2/2006 | Harjunmaa et al. | |
| 7,016,713 B2 | 3/2006 | Gardner et al. | |
| 7,627,357 B2 | 12/2009 | Zribi et al. | |
| 2002/0072676 A1 | 6/2002 | Afanassieva | |
| 2002/0183624 A1 * | 12/2002 | Rowe et al. | 600/476 |
| 2003/0144582 A1 * | 7/2003 | Cohen et al. | 600/316 |
| 2004/0077972 A1 | 4/2004 | Tsonton et al. | |
| 2004/0138539 A1 | 7/2004 | Jay et al. | |
| 2005/0033127 A1 | 2/2005 | Ciurczak et al. | |
| 2005/0159658 A1 * | 7/2005 | Jeon et al. | 600/316 |
| 2005/0171413 A1 | 8/2005 | Blair | |
| 2007/0049809 A1 | 3/2007 | Bechtel et al. | |
| 2007/0073118 A1 | 3/2007 | Ridder et al. | |
| 2007/0260131 A1 * | 11/2007 | Chin | 600/323 |

OTHER PUBLICATIONS

Ver Steeg, Benjamin et al.; "Photonics technology enables accurate, noninvasive alcohol testing. A New Eye on Law Enforcement," *SPIE'S oemagazine*, Jun./Jul. 2005, pp. 26-28.

Burmeister, Jason J. et al.; "Evaluation of Measurement Sites for Noninvasive Blood Glucose Sensing with Near-Infrared Transmission Spectroscopy," *Clinical Chemistry 45*, vol. 9; 1999, pp. 1621-1627.

* cited by examiner

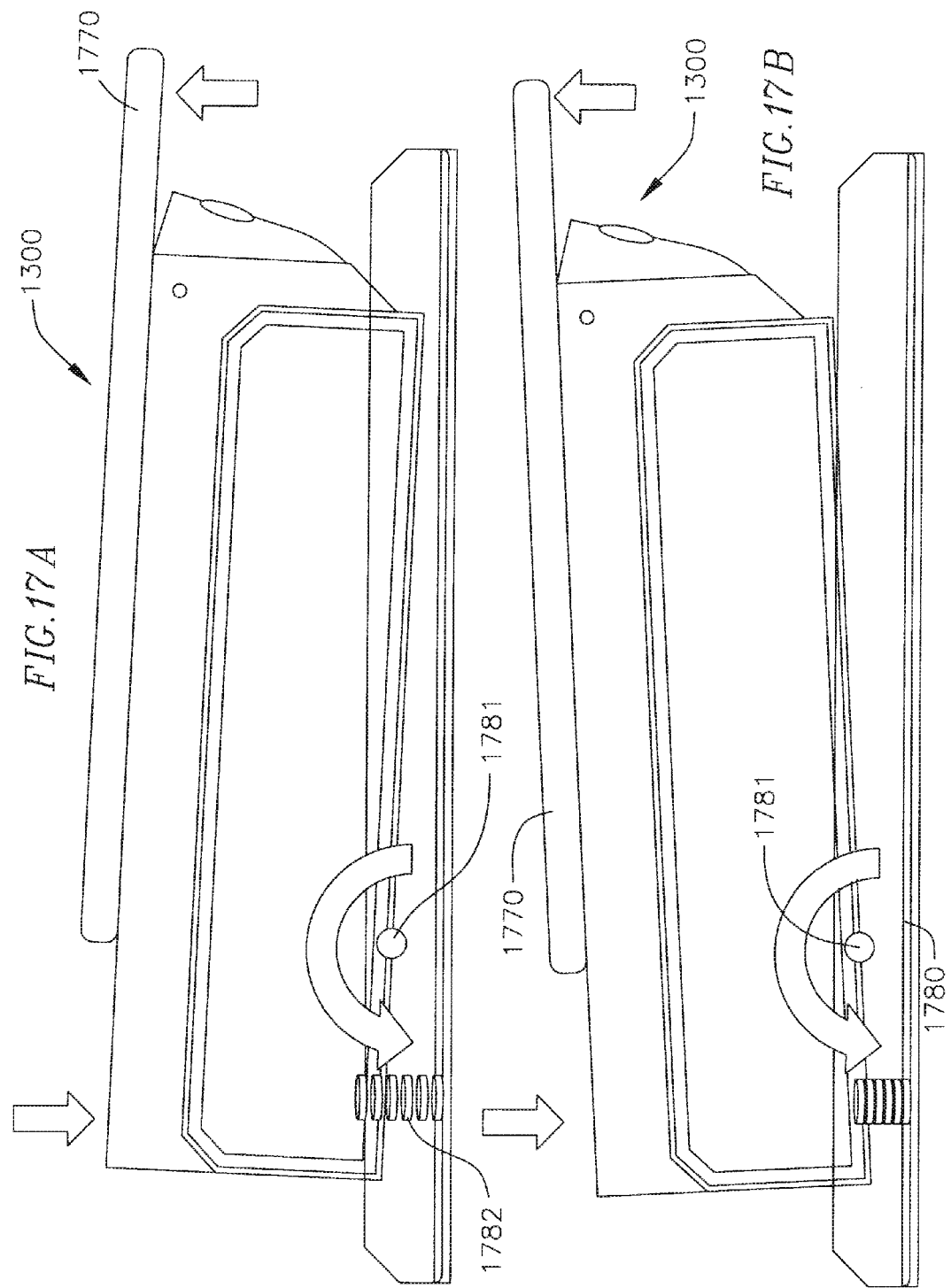

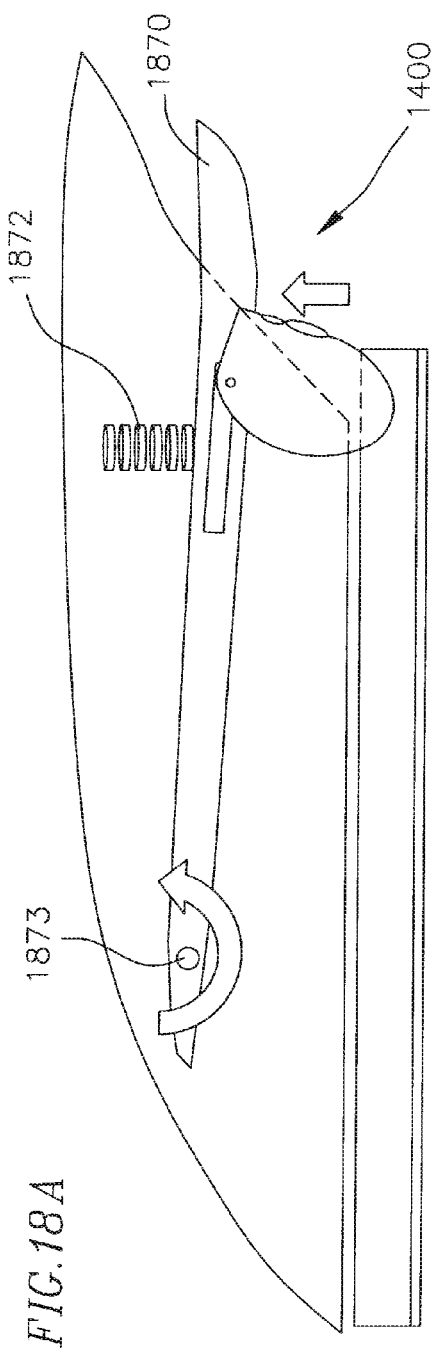
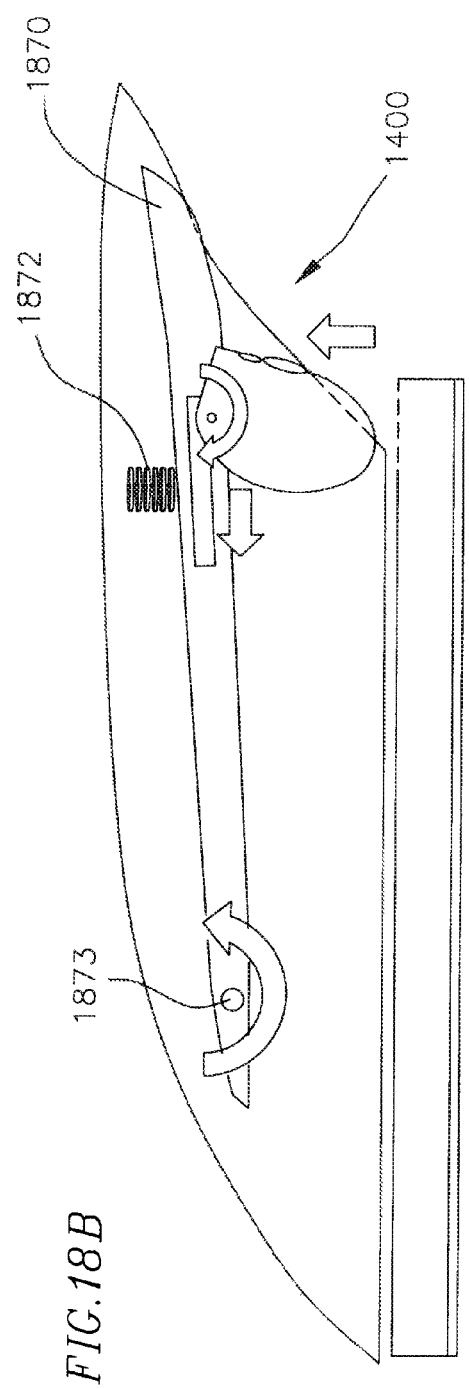
FIG.18A
FIG.18B

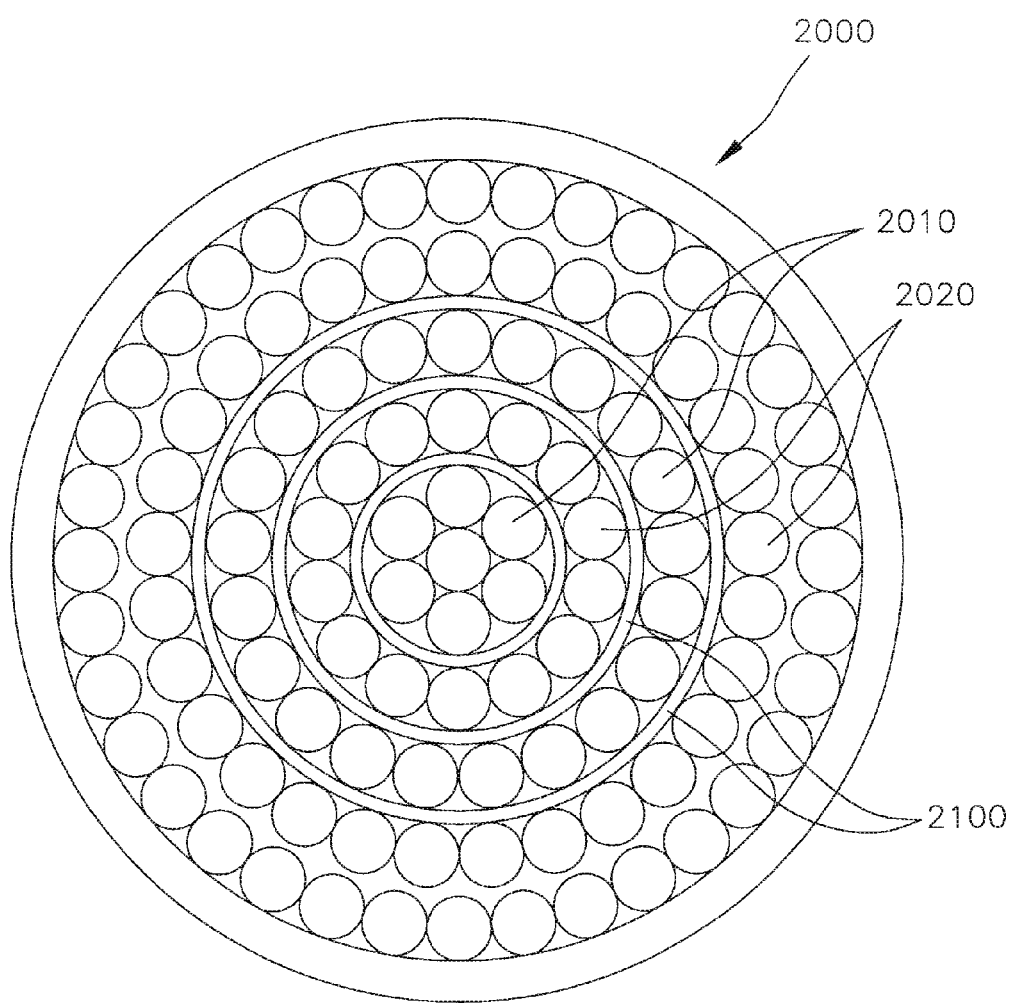

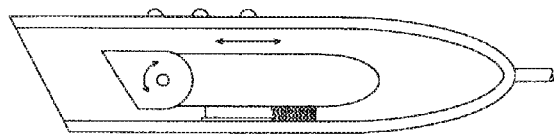
FIG. 28
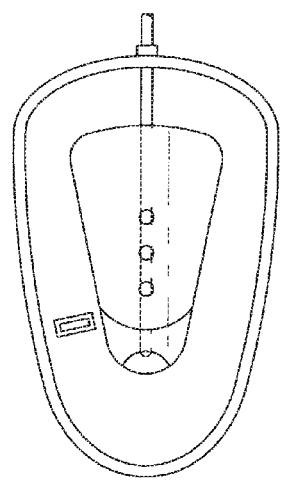
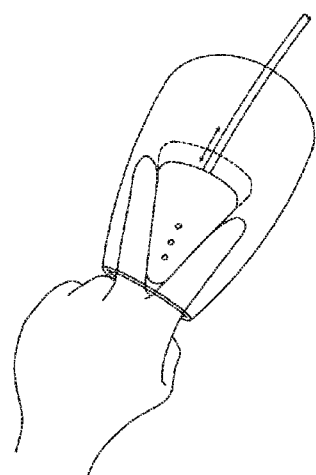
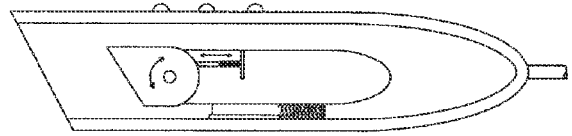
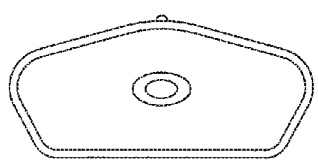
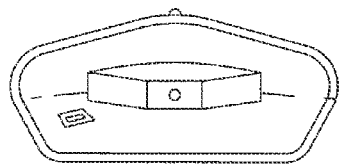
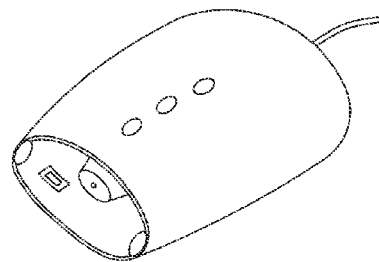
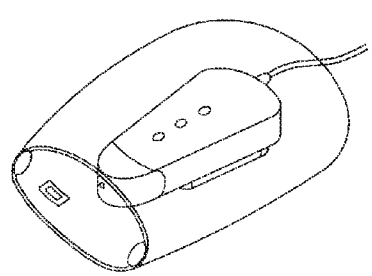

APPARATUS FOR NON-INVASIVE SPECTROSCOPIC MEASUREMENT OF ANALYTES, AND METHOD OF USING THE SAME

CROSS-REFERENCE TO RELATED APPLICATION(S)

This application claims priority to and to the benefit of U.S. provisional patent applications Ser. No. 60/949,836 filed Jul. 13, 2007 and Ser. No. 60/966,028 filed Aug. 24, 2007, the contents of which are incorporated herein by reference. This application also contains subject matter that is related to the subject matter in U.S. Ser. No. 11/702,806, the content of which is cited and incorporated by reference.

FIELD OF THE INVENTION

This invention relates generally to a spectroscopic system for the non-invasive evaluation of bodily fluids of a subject. In particular embodiments, it may be used for measurement of components of or analytes in human blood, such as alcohol or its metabolic byproducts. It may also be coupled with other indicators such as a biometric acquisition system, temperature indication system, a touch and/or pressure sensor.

SUMMARY OF THE INVENTION

Aspects of embodiments of the present invention are directed toward a method and an apparatus for non-invasively evaluating bodily fluids of a subject.

The method for non-invasively evaluating bodily fluids of a subject may include providing a source of electromagnetic radiation to a device, positioning the device at an interstitial location between fingers or toes of a subject, and receiving the electromagnetic radiation reflected from the subject.

In an aspect of an embodiment of the present invention, the method includes applying the device to a surface of the subject at a substantially constant pressure, and the device can be applied such that it is to be substantially flush with the surface of the subject. The device may also include a touch and/or other type of sensor to activate the device and/or a pressure sensor to ensure that the device is operated at a particular pressure.

In an aspect of an embodiment of the present invention, the device is applied at a substantially constant pressure between first (index) and second (middle) fingers of the subject, or between first and second toes of the subject.

In an aspect of an embodiment of the present invention, the device is a probe.

In another aspect of an embodiment of the present invention, the probe includes a probe base and a probe head.

In an aspect of an embodiment of the present invention, the electromagnetic radiation is near infrared radiation.

Another aspect of an embodiment of the present invention is directed toward an apparatus for non-invasively evaluating bodily fluids of a subject including a means for providing a source of electromagnetic radiation to a device, a means for positioning the device at an interstitial location between fingers or toes of the subject, and a means for receiving the electromagnetic radiation reflected from the subject.

In an aspect of an embodiment of the present invention, there is provided a means to apply the device to a surface of the subject at a substantially constant pressure. The means may use a biasing member that exerts a substantially constant pressure, and/or a pressure sensor that ensures that the apparatus operates at a particular pressure.

In an aspect of an embodiment of the present invention, the apparatus is adapted to be positioned in the interstitial location, between first and second fingers of the subject. In another embodiment, the apparatus is applied so that is substantially flush with a surface of the subject.

In an aspect of an embodiment of the present invention, the means for providing a source of electromagnetic radiation to the device is a near infrared radiation source.

Another aspect of an embodiment of the present invention is directed toward an apparatus for non-invasively evaluating bodily fluids of a subject including a probe, a mounting support for the probe that defines at least one path, and a biasing element, where the probe is movable along the at least one path in a direction away from an initial point, and the probe is biased by a substantially constant force exerted by the biasing element toward the initial point. A pressure sensor may also be used to ensure that the apparatus is used at a particular pressure.

In an aspect of an embodiment of the present invention, the probe includes a probe head and a probe body, where the probe body having a proximal end and a distal end, and the probe head is pivotally attached to the probe body.

In another aspect of an embodiment of the present invention, the probe is also movable up and down along a second path that is substantially orthogonal to the at least one path. In one embodiment, the biasing element is a coil spring.

Another aspect of an embodiment of the present invention is directed toward a probe for non-invasively evaluating bodily fluids of a subject including a source of electromagnetic radiation, a probe head, at least one fiberoptic for conveying electromagnetic radiation from the source to the probe head, a detector, and at least a second fiberoptic for conveying electromagnetic radiation reflected from the subject to the detector, where the probe head is adapted to be received at an interstitial location between fingers or toes of the subject.

In an aspect of an embodiment of the present invention, the probe is biased toward the interstitial location by a substantially constant force. A sensor may also be employed to ensure that the probe is operated at a particular force.

In another aspect of an embodiment of the present invention, the probe head is pivotable so that it can be applied flush against a surface of the subject.

In another aspect of an embodiment of the present invention, the probe head is adjustable up and down relative to the interstitial location.

In another aspect of an embodiment of the present invention, the probe includes a source of electromagnetic radiation that generates near infrared radiation.

Another aspect of an embodiment of the present invention is directed toward a fiberoptic member for use in spectroscopic measurements including a plurality of source fiberoptic strands adapted to convey electromagnetic radiation from a source of electromagnetic radiation to a device, a plurality of detector fiberoptic strands adapted to receive and convey electromagnetic radiation from the device to a detector, where the plurality of fiberoptic strands and the plurality of other fiberoptic strands combined into a single fiberoptic bundle at the device. In one embodiment, at least some of the detector fiberoptic strands in the fiberoptic bundle are arranged in a double row along an outer periphery of the source fiberoptics.

In an aspect of an embodiment of the present invention, the single fiberoptic bundle is adapted to be received at an interstitial location between fingers or toes of a measurement subject.

In an aspect of an embodiment of the present invention, the fiberoptic member also includes a temperature measurement device.

In an aspect of an embodiment of the present invention, the source of electromagnetic radiation of the fiberoptic member generates near infrared radiation.

In one embodiment, the temperature measurement device is an infrared device.

BRIEF DESCRIPTION OF THE DRAWINGS

FIGS. 17A and 17B are a series of side views depicting a vertical movement of a probe created by a spring mechanism according to an embodiment of the present invention.

FIGS. 18A and 18B are a series of side views depicting a translational movement, a rotational movement, and a vertical movement of a probe according to an alternative embodiment of the present invention.

FIG. 20 illustrates a cutaway view of a probe head with multiple source fiberoptics and detector fiberoptics according to another aspect of an embodiment of the present invention.

FIG. 28 illustrates multiple views of different aspects of embodiments of the present invention.

DETAILED DESCRIPTIONS

Figure 1:
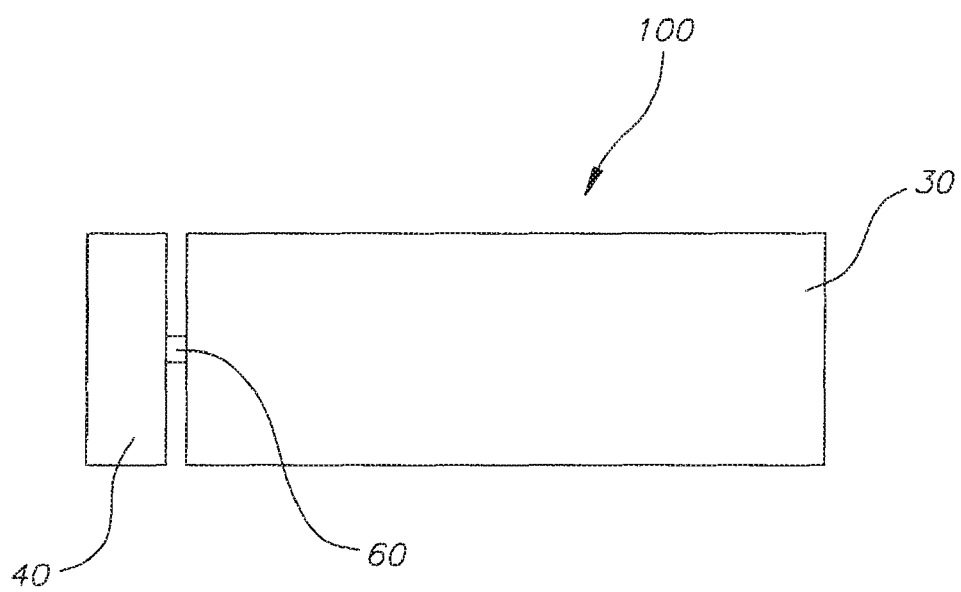
FIG. 1 illustrates a side view of a probe having a probe head, a probe base, and a biasing mechanism connecting the probe head to the probe base according to an aspect of an embodiment of the present invention.

An apparatus for non-invasive spectroscopic measurement according to one embodiment of the present invention is suitable for many applications, particularly for non-invasively evaluating bodily fluids such as monitoring blood components of or blood analytes in a subject. The apparatus might also be used to detect synthetic markers or nano-particles that have been coupled to certain components or analytes in a bodily fluid of a subject, such as the subject's blood, where the markers or nano-particles are designed to have a particular spectroscopic signature. In addition, the apparatus could be used to detect toxins or hazardous chemicals in bodily fluids.

Such an apparatus can be useful in biomedical applications. For example, the apparatus could be used to monitor blood glucose level for diabetics. It could also be used to monitor lactic acid levels for detecting shock in hospital patients. In such applications, the apparatus could be configured to be attachable to a patient for continuous monitoring. When coupled with a biometric identification device, the apparatus could also link to insurance and/or medical records of a patient. This link could be used to update patient information or to make comparisons to past spectroscopic readings as an aid in diagnosis and treatment.

Such an apparatus can also be useful in security applications. For example, the apparatus can be implemented to regulate access to buildings, manufacturing sites, or other secured areas, or to restrict the operation of equipments, cars, boats, aircrafts, or other vehicles by those who are under the influence of alcohol or other substances. The apparatus can also be implemented as a bio-monitoring device, for example, the apparatus can be configured to determine a bio-condition of an operator, which can be used to determine whether the operator is impaired to perform certain duties.

The apparatus includes a source of radiation. In one embodiment, the radiation is an electromagnetic radiation. The apparatus is configured to safely administer the radiation to the subject's body and to receive electromagnetic radiation being reflected back from the subject. In one embodiment, a fiberoptic bundle is used to administer and receive the light (electromagnetic radiation), such as infrared light electromagnetic radiation. Further, the apparatus may include an acquisition system that analyzes the received electromagnetic radiation resulting from interactions with the subject's body.

In one embodiment, a quartz halogen lamp is used to provide a source of electromagnetic radiation in the near infrared region. The near infrared region of the spectrum is suitable for noninvasive measurement of concentrations of blood components or blood analytes, such as alcohol content because of the relatively good light transmission of skin tissues at these wavelengths. While a quartz halogen lamp has been described in connection with providing a radiation source for measuring blood alcohol content according to an embodiment of the present invention, it is to be understood that the invention is not limited to the disclosed embodiment, but, on the contrary, is intended to cover various modifications and equivalent substitutions thereof. For example, other light producing devices such as flash lamps, light emitting diodes, quartz-halogen, and/or tungsten-halogen light sources can be used in conjunction with filtering mechanisms to produce a certain spectral range that corresponds to the spectral range absorption of other targeted tissue components or analytes to be measured.

In one embodiment, the apparatus includes a device that contains the radiation source and the acquisition system. The device can be in various shapes such as cylindrical, cuboid, spherical, trapezoidal, or any combination thereof so long as it is suitable to be pressed flush against the subject's testing area or accommodate an interstitial location between fingers or toes of the subject. In one embodiment, the device is a probe.

FIG. 1 illustrates a device or probe 100 according to an embodiment of the present invention. Referring to FIG. 1, probe 100 includes a probe head 40 and a probe base 30. Probe 100 may also include a biasing mechanism 60 that connects probe head 40 to probe base 30.

Figure 2:
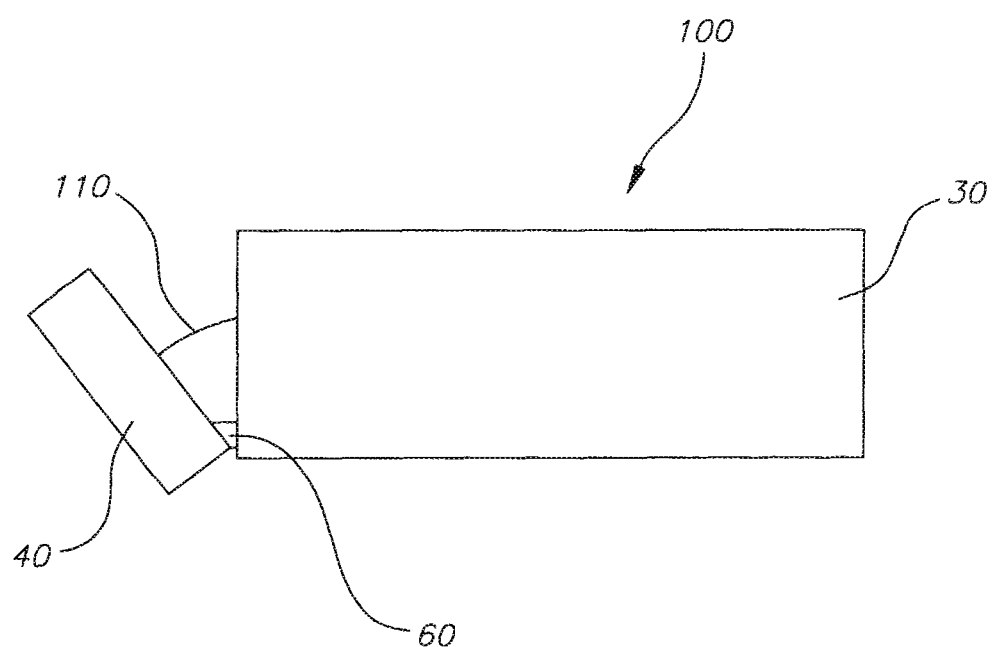
FIG. 2 illustrates a side view of another probe with a biased hinge mechanism connecting a probe head to a probe base according to one embodiment of the present invention.

FIG. 2 illustrates probe 100 having a spring biased hinge 110 according to an aspect of an embodiment of the present invention. Referring to FIG. 2, probe head 40 of the apparatus is fastened to probe base 30 by way of spring biased hinge 110, which allows rotational movement to occur about the probe head in a vertical plane. Spring biased hinge 110 allows the probe head to exert a consistent pressure against the subject's testing area. Of course, it should be understood that a biasing means other than the spring may be used.

Figure 3:
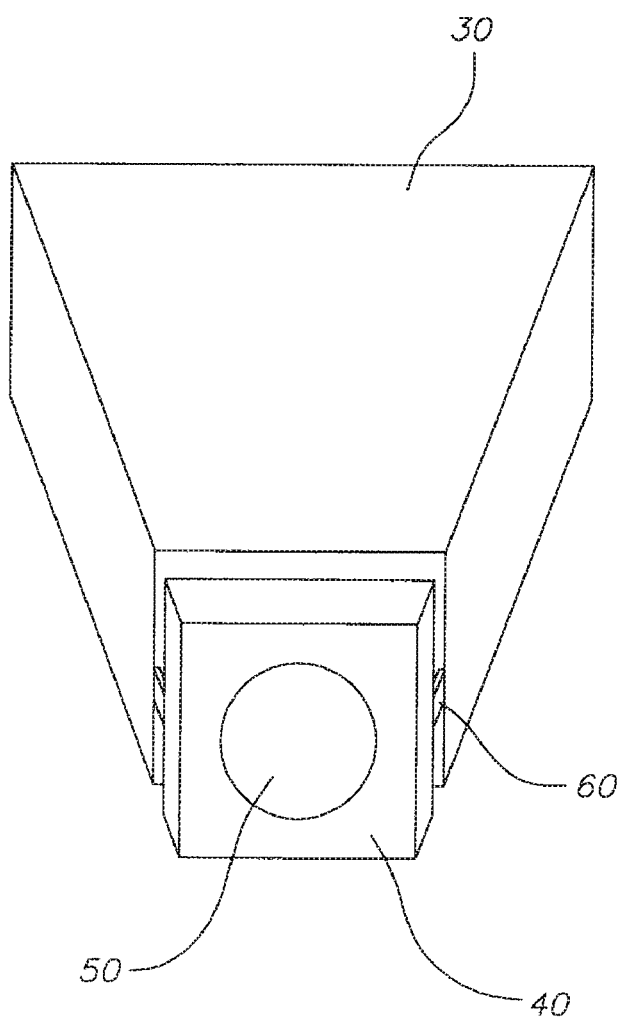
FIG. 3 illustrates a front view of a probe head and a probe base according to another aspect of an embodiment of the present invention.
Figure 4:
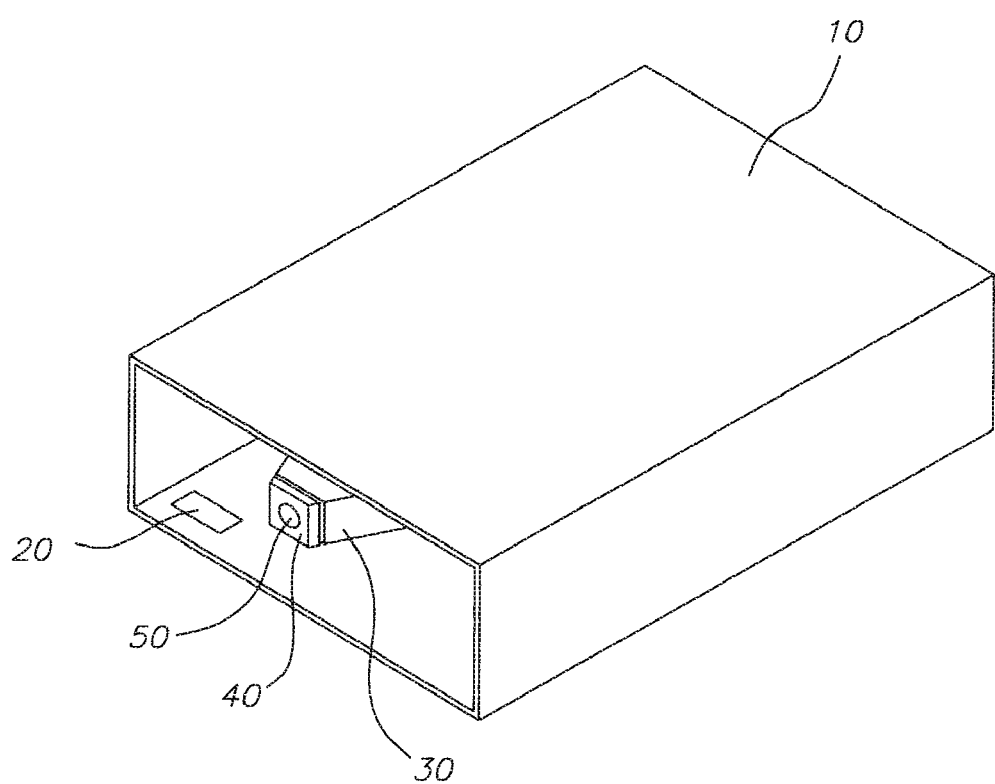
FIG. 4 illustrates a diagram of a housing that contains a probe head, probe base, and a biometric sensor according to an aspect of an embodiment of the present invention.

FIG. 3 illustrates a probe with probe head 40 and probe base 30 being trapezoidal (or pie-like) in shape according to one embodiment of the present invention. Although a trapezoidal shape is shown, probe head 40 and probe base 30 may exhibit other shapes, such as, for example, rectangular, cylindrical or any other ergonomically appropriate shape. Probe head 40 further includes at least one fiberoptic bundle 50 for spectroscopic measurement. Probe base 30 can be configured to support fiberoptic bundle(s) and at the same time provide translational movement to the unit. In this way, probe 30 can provide reproducible and uniform spectroscopic measurements.

FIGS. 4-10 illustrate various forms of an apparatus having a housing 10 configured to house probe base 30 and probe head 40 according to various embodiments of the present invention. Housing 10 of the apparatus is configured to allow the apparatus to be mounted to various locations or surfaces such as, for example, inside of a vehicle or on a wall near an entry point. In this way, the apparatus can provide the testing of blood components or blood analytes, such as, for example, blood alcohol at various locations. In addition to providing protection, housing 10 can also be configured to accommodate additional features such as biometric verification, temperature measurement systems, touch activation and/or pressure sensors.

FIGS. 4-7 illustrate an apparatus that includes a biometric verification system 20 according to embodiments of the present invention. Biometric verification system 20 provides biometric verification by performing a finger and/or toe print scan. Other forms of biometric scan could also be incorporated into the apparatus. For example, a palm scan or other form of palm recognition system could be incorporated while still allowing spectroscopic testing at an interstitial location on a subject's hand. Similar to the blood component or blood analyte acquisition system of probe 100, the biometric verification system 20 can prevent operation of a vehicle if the subject's biometric authentication does not indicate an authorized user. Results of the biometric scan and spectroscopic measurement can be stored in a system for a selected number of users and for a determined period of time. As noted above, this information can also be linked to a database of patient information for use in diagnosis and treatment and/or to a database relating to vehicle, building, equipment, etc. access.

Figure 8A:
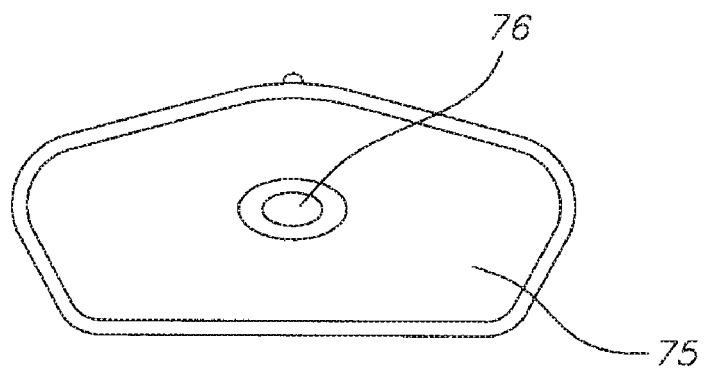
FIGS. 8A and 8B illustrate rear and front views, respectively, of a probe according to an embodiment of the invention.
Figure 8B:
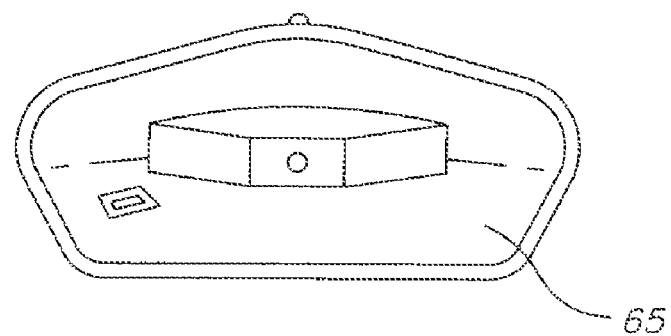

In an embodiment of the present invention, housing 10 is smoothly contoured and in an oval shape (FIGS. 5-8), resembling a computer mouse. Housing 10 may also have other shapes. Housing 10 can have an open end 65, as shown in FIG. 8B, to receive a subject's fingers or toes and a closed end 75, as shown in FIG. 8A, with an opening 76 for receiving a power interface such as a power cord.

In one embodiment, housing 10 is about 110 mm in length, 70 mm in width at the open end, and 90 mm in width at the closed end.

In an embodiment of the present invention, a probe body is smoothly contoured with grooves (not shown) on two side walls adapted to receive a first finger and a second finger of a testing subject.

According to an embodiment of the present invention, both the probe body and housing 10 are smoothly contoured to enable the subject's finger, fingers, hand, toe, toes, or foot to enter the housing without binding, pressing, or pulling the skin in or near the region of the subject that is to be measured. Binding of the skin may create a fold or non-smooth surface of the subject's skin, which may interfere with acquisition of the signal from the subject due to variation of the subject's skin density, consistency or depth. Similarly, stretching or pulling of the subject's skin created by the housing may interfere with acquisition of the signal from the subject due to variation of the subject's skin density, consistency, or depth. The smooth surface of the housing minimizes the pressure and friction exerted on the subject's skin, and lessens the effect of the housing pulling, pressing, stretching, or compressing the subject's skin. As a result, the pressure on the subject's skin is applied by probe head 40 in a manner that results in a reproducible pressure from the probe head onto the subject's skin.

Figure 5:
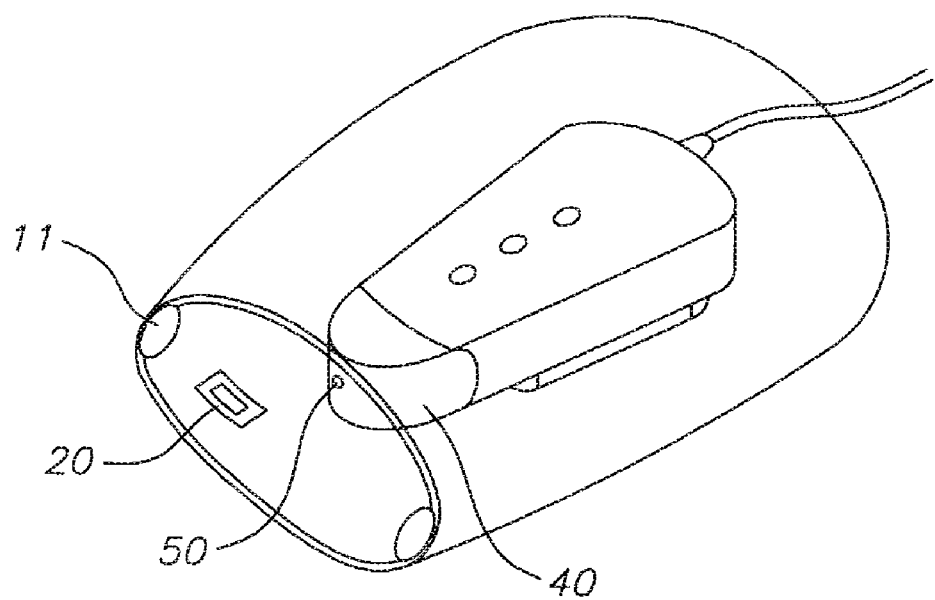
FIG. 5 illustrates a cutaway view of a housing that contains a probe according to an embodiment of the invention.
Figure 6:
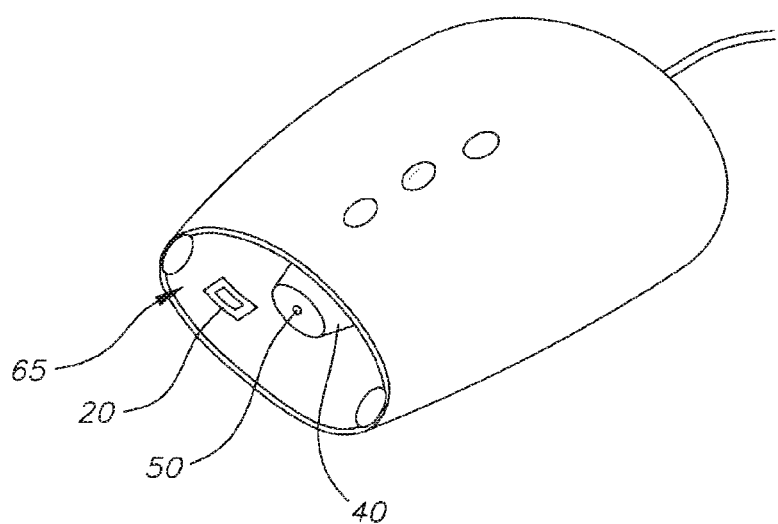
FIG. 6 illustrates another view of a probe according to an embodiment of the invention.
Figure 7:
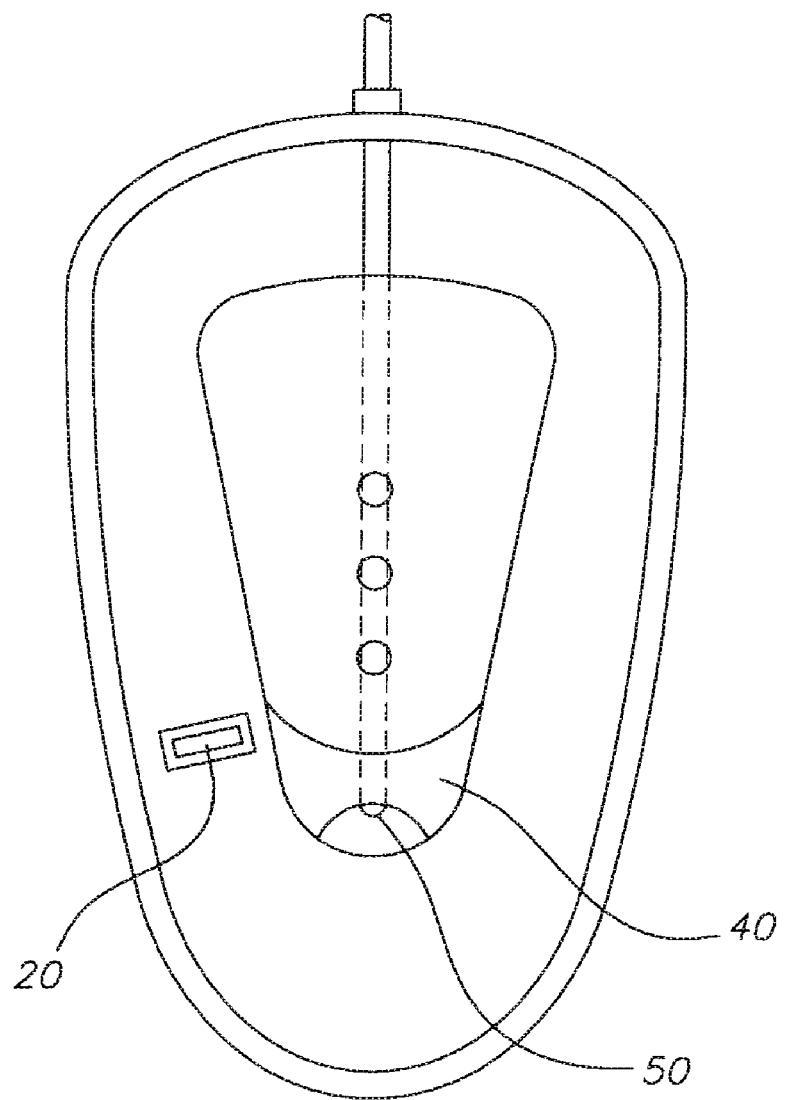
FIG. 7 illustrates a cutaway top view of a probe according an embodiment of the invention.

Referring to FIG. 5, the housing of the apparatus, according to an embodiment of the present invention, further includes side pads 11 to enable and/or facilitate reproducible blood flow to the region of the subject that is to be spectroscopically measured. These pads, for example, could be heating and/or cooling pads so that temperature adjustment could be used to create an optimal or consistent temperature at which measurements are made. The location of one or more heating and/or cooling pads could also be other than at the sides of the housing. For example, pads could be positioned centered at the top and bottom of the housing opening so as to be in closer proximity to the testing area for quicker temperature adjustment. The pads may operate through conductive, convective or radiation heating and/or cooling. Variations in the subject's blood flow in the region spectroscopically measured may affect the accuracy or precision of the measurements obtained. The structure of housing entry may seek to minimize the effects on the subject's blood flow to the region being measured, or it may work to produce an effect on the blood flow of that region. The pads may also be used to stabilize the region to be tested. For example, they could help to hold a subject's hand still during testing. The housing is designed to produce reproducible or consistent effects on the subject's blood flow. These effects may be achieved passively or actively.

In one embodiment, an entry 65 of the housing is designed to passively allow minimal alteration to the subject's blood flow, leaving the probe head to control the pressure exerted on the subject's skin. Accordingly, the width of entry 65 is designed to have gradual angles and smooth contours, see FIG. 7 for example. The shape of the housing can have other shapes such that it provides consistent blood flow to the region of the subject to be spectroscopically measured would be suitable for the present invention, including mechanisms that actively regulate the subject's blood flow for accurate, precise, or reproducible measurements.

Figure 14:
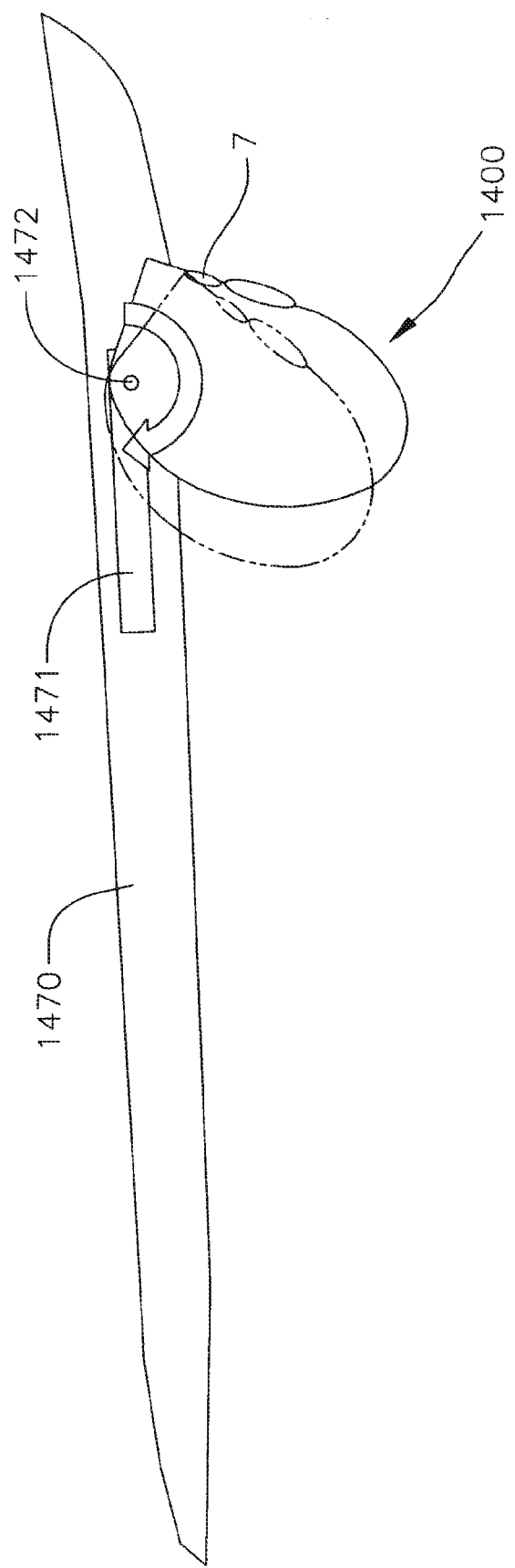
FIG. 14 illustrates a cutaway side view that depicts a rotational movement of a probe according to an alternative embodiment of the present invention.
Figure 15:
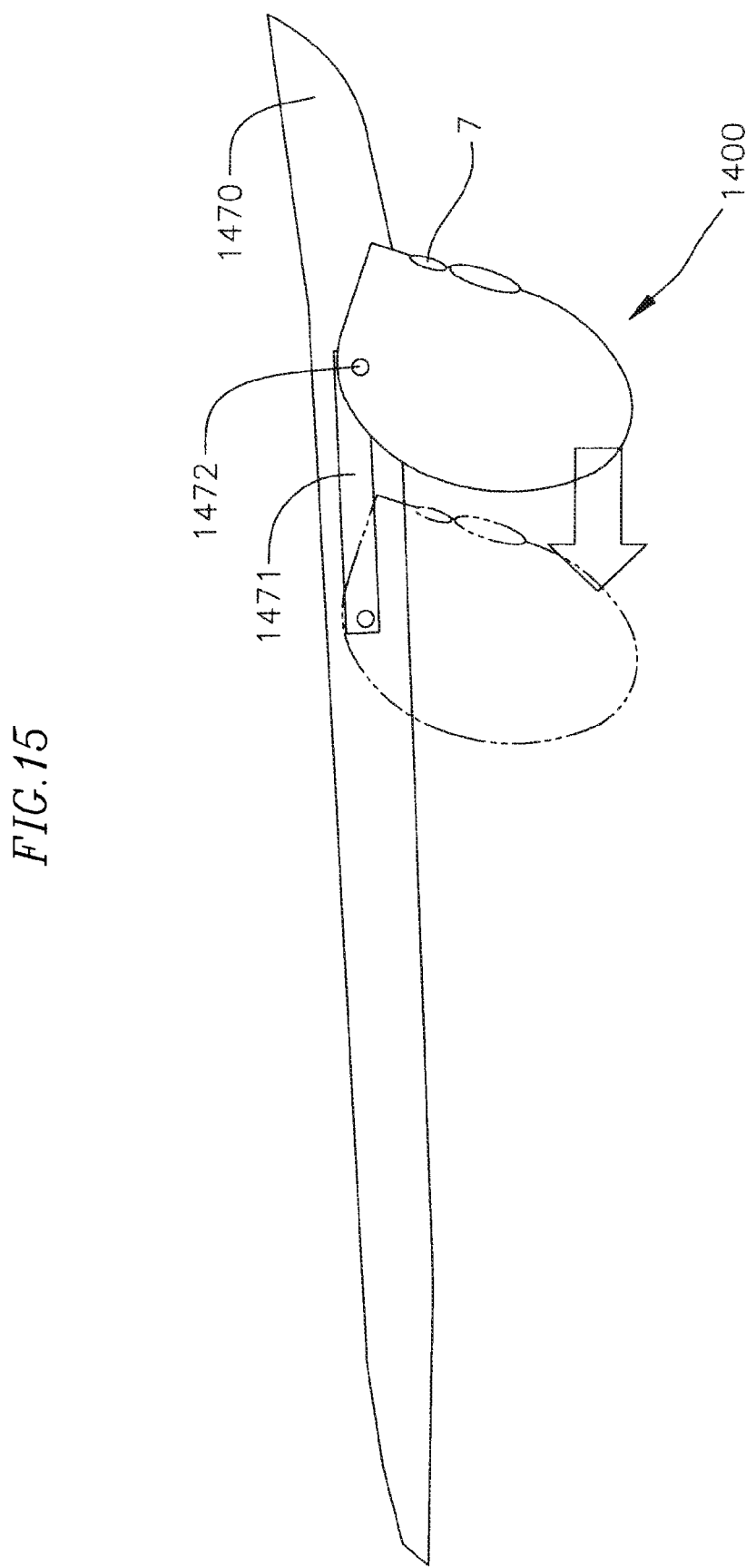
FIG. 15 is a series of side cutaway views that depicts a translational movement of a probe, where the translational movement being along a translational guide according to an alternative embodiment of the present invention.

In some embodiments, the source of radiation may always be on so that the apparatus is ready for use at any time. In other embodiments, it may be appropriate to have the source of radiation turned off while not in use. In such embodiments, a means for activating the source of radiation and/or otherwise preparing a device for use will be needed. Various means may be used. A touch sensor may be used so that the device turns on as soon as a subject touches part of the device. A capacitance or resistance touch switch may be used to create a touch sensor. Alternatively, a temperature sensor that detects the presence of a subject could be used to activate the device. Remote sensors such as those detecting movement toward a device or movement in the vicinity of a device could also be used for activation. Such sensors may be located in a probe head in a location proximate to the source of radiation. For example, FIGS. 14 and 15 depict a sensor 7 positioned just above the radiation source. It should be understood, however, that the sensors can be positioned in other locations as appropriate for their specific function.

Operator action could also be used to activate a device. An operator could press a wireless or wired switch to trigger activation. For example, for a device installed in a vehicle, a keyless entry system could be used to also activate the device. A device in a vehicle could also be activated through opening of a vehicle door, by pressure detected on the driver seat of the vehicle or by other means detecting the presence of an operator. Voice or sound activation systems may also be used so that an operator can provide a voice command, a clap or other sound to turn on a device for testing.

Initial operator interaction with a device may also be used to activate a radiation source or otherwise trigger the device to proceed with a spectroscopic measurement. As noted above reproducible pressure is important to achieving reproducible measurements. Thus, a device could incorporate a pressure sensor that detects the pressure with which a subject is placing the region to be tested against a probe on the device. When a predetermined pressure is measured, this may then trigger the device to activate and take a spectroscopic reading.

As discussed in greater detail below, the device interface with a subject may be optimized by having a probe that is moveable in one or more directions and/or subject to a constant biasing pressure on movement in those one or more directions. Accordingly, position and/or pressure sensors may be incorporated into the device and the device then programmed to wait until all the sensors detect the subject to be in an optimal position and/or pressure condition before it activates spectroscopic measurement. In addition, all parameters measured by the sensors could be recorded and stored by the device during spectroscopic measurement for use in controlling future use/activation of the device or for use as additional data to be taken into account in evaluating the results of the spectroscopic measurement.

Components & Movements

FIGS. 5 through 10 depict a variety of housing configurations for a spectroscopic measurement device having a row of indicator lights located on the top of the housing. These indicator lights may be used in conjunction with a pressure sensor to help provide for consistent spectroscopic measurements. Although translational movement, pivoting and/or height adjustment of a probe in the spectroscopic measurement device are presently preferred as described in greater detail below, even without any movement of a probe a pressure sensor could be used to help provide for more consistent measurement. As noted above, a pressure sensor could be used to trigger measurement at an optimal or present pressure being exerted on the probe. In addition, the indicator lights may be used to provide visual feedback to a user of when the pressure is appropriate. That is, one indicator could be a red light that flashes when the pressure is too low or too high. Another indicator could be a yellow light that flashes when the proper pressure is being approached. The third indicator could be a green light that flashes when the pressure is within acceptable limits for measurement. For systems that require warm up time, the indicator(s) could be used to indicate when the system is ready for use. Of course, other indicator signals could be used. For example, an audible signal could be used to communicate to a user when the pressure being exerted is appropriate. The indicator may also use an LED or LCD display and/or use the existing lights or communication devices (horn, speakers, etc.) on a vehicle or in a building. The pressure sensors and indicators may also be used in the context of any of the moveable devices described below.

According to some embodiments of the present invention, various components of probe 100 are configured to provide translational and/or rotational movements. In this way, consistent spectroscopic measurements can be achieved by probe 100.

In one embodiment, probe head 40 is configured to provide translational movement by having one end being biased by an axial spring.

Figure 9:
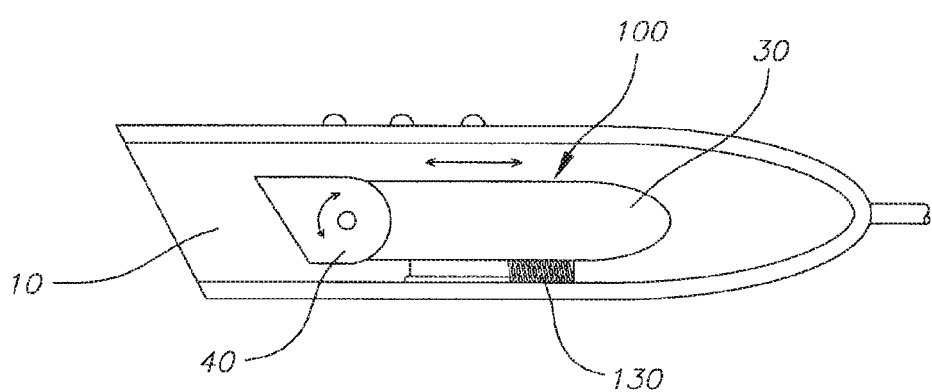
FIGS. 9-10 illustrate cutaway side views of one or more probes according embodiments of the present invention.

FIG. 9 illustrates a probe having a biasing member 130 according to an aspect of an embodiment of the present invention. Translational movement is provided to the probe base 30 by attaching probe base 30 to biasing member 130, where the biasing member 130 is biased against a structure such as a portion of the housing 10.

As shown in FIG. 9, biasing member 130 is an axial spring attached to the lower side of the probe base 30 and to a bottom wall portion of housing unit 10. The axial spring provides a constant force that pushes the whole probe toward an initial testing point. The spring coil allows both the probe base 30 and the probe head 40 to move translationally along a path that is parallel (or substantially parallel) to the probe body and away from the initial testing point. In the embodiment of FIG. 9, the probe head may be pivotably attached to the probe base so that it can pivot freely to conform to the surface of the testing region.

In other embodiments, both probe base 30 and probe head 40 are spring biased to provide translational as well as rotational movement under pressure. In this way, not only consistent pressure is provided, a flush contact of probe head 40 against the subject's tissue assisted by pressure for even better spectroscopic measurements. One or more touch sensors (such as sensor 7, see FIGS. 14 and 15) may also be used on the probe head to assess whether the probe head is flush with the subject before measurement is taken.

Figure 11:
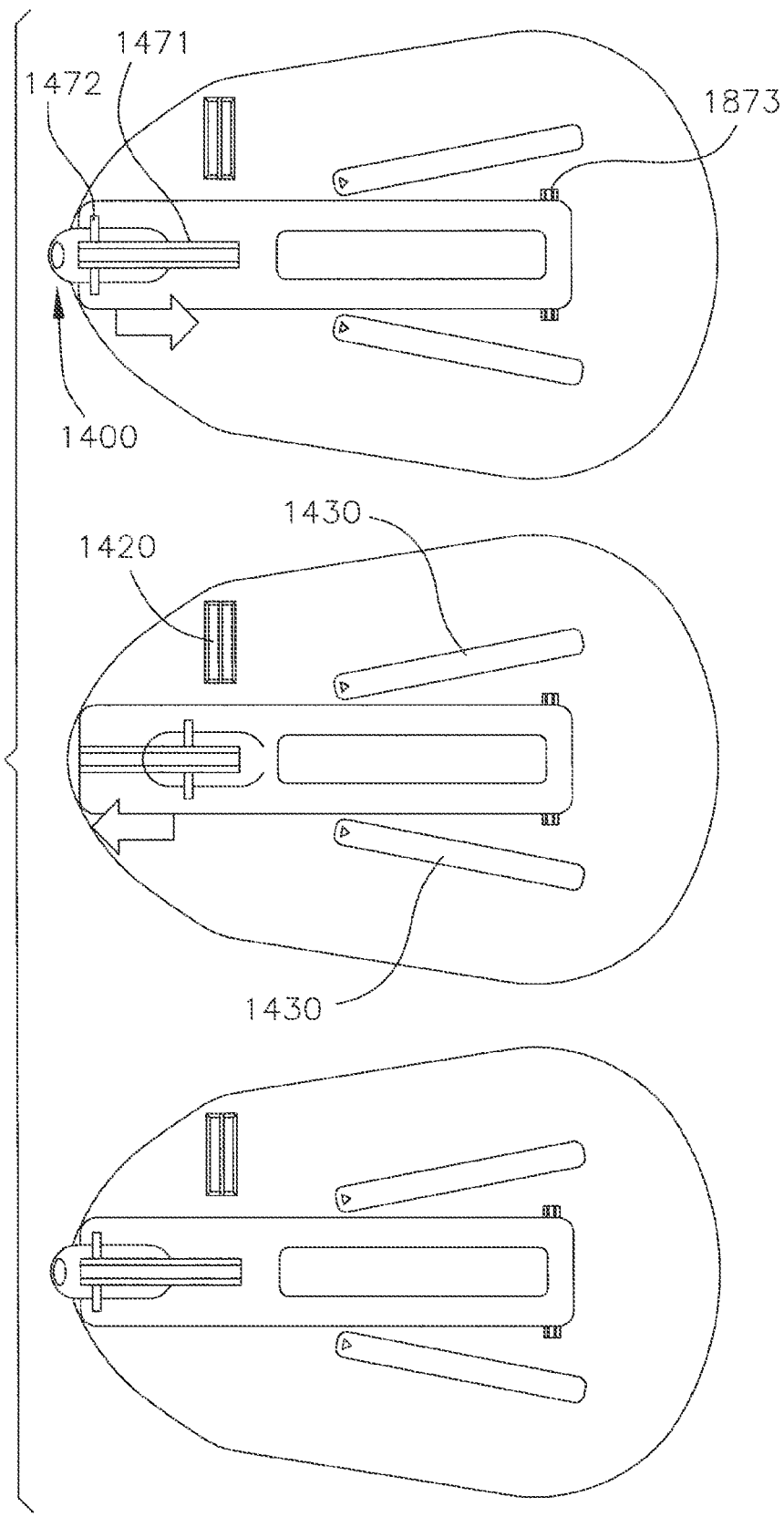
FIG. 11 illustrates a series of top views that depict a translational movement of a probe according to an alternative embodiment of the present invention.

FIGS. 14 and 15 illustrate a probe 1400 having both translational and rotational movement according to an embodiment of the present invention. Translational movement is provided to probe 1400 by attaching probe 1400 to a biasing member, where the biasing member urges the probe toward an initial testing position with a substantially constant force. FIG. 11 shows a series of top views of probe 1400 in a housing wherein translational movement of the probe is depicted. FIG. 11 also shows the relative placement of a biometric scanner 1420 and finger guide walls 1430 that will guide the fingers of a user apart and position the user's interstitial region at the front of probe 1400. Rotational movement is provided to the probe 1400 by having the probe 1400 pivotally connected to a guiding slot 1471 by a first probe pin 1472. Probe pin 1472 causes probe 1400 to pivot about the pin from an initial contacting position to a final contacting position at an angle. In one embodiment, the angle is an acute angle. Slot 1471 may contain a biasing member, such as a spring, that acts against translational movement of the probe. Slot 1471 may also contain a pressure gauge, such as a load cell or a gas cylinder, that senses the pressure being exerted on the probe. This pressure sensor could then be used to activate the device or indicate optimal pressure as described above. A biasing member such as a spring, may also be incorporated in or associated with pin 1472 that acts against rotations of the probe.

Figure 10:
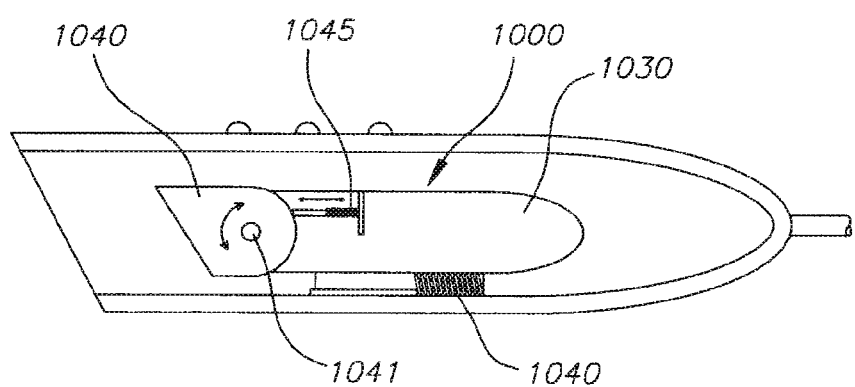

FIG. 10 illustrates a side view of probe 1000 according to an aspect of an embodiment of the present invention. Probe 1000 may exhibit some or all of the features of probe 100 described above. Referring to FIG. 10, probe 1000 with a probe base 1030 and a probe head 1040, each of which have a proximal end and a distal end. In this embodiment, the rotational movement of the probe head 1040 is opposed by having a spring mechanism 1045 attached between the distal end of the probe head 1040 and the proximal end of probe base 1030.

At a non-engaging stage, the probe head 1040 is rotated toward the front and is resting at an initial contacting position, and probe 1000 is resting at an initial testing position. At an engaged stage, as a subject's body part is pressed against probe head 1040, probe head 1040 may rotate or pivot from the initial contacting position to a final contacting position to accommodate the subject's testing area by pivoting about a probe pin 1041. The rotation of the probe head is provided to ensure that fiberoptic bundle 50 of probe head 1040 can be positioned flush (or to substantially flush) against the subject's testing area for better spectroscopic measurements. At the same time, the probe 1000 may be pushed back against axial spring 1045, or axial spring 1130, or both causing probe 1000 to move from the initial testing position to a final testing position.

Alternatives to an axial spring to provide translational movements would include, but are not limited to, mounting probe base 1030 or the probe head 1040 on ball bearings and at an inclined angle to harness gravity to supply the consistent pressure, or to use a gas filled piston.

Figure 12:
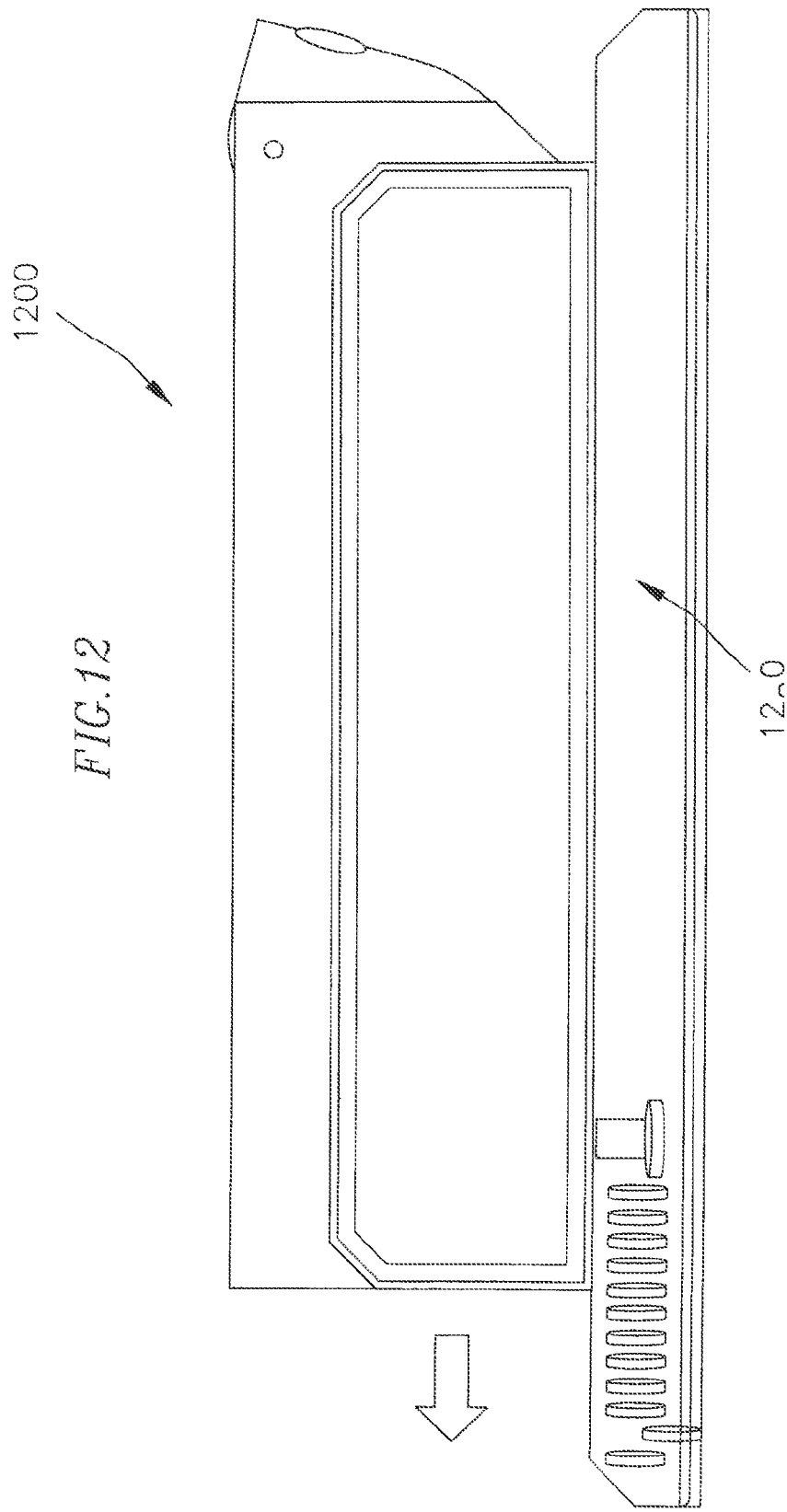
FIG. 12 illustrates a side view that depicts a translational movement of a probe according to an embodiment of the present invention.

FIGS. 12 and 15 illustrate side views of two probe assemblies according to aspects of embodiments of the present invention.

FIG. 12 illustrates a probe 1200 having a translational movement according to an embodiment of the present invention. Probe 1200 may exhibit some or all of the features of probe 100 or any probe described above. The translational movement is created along a path that is substantially parallel to a bottom supporting member 1280, where it is created by a spring mechanism mounted toward the back of a bottom supporting member 1280.

FIG. 15 also shows a probe 1400 having a translational movement according to an aspect of an embodiment of the present invention. Similar to probe 1200, probe 1400 may exhibit some or all of the features of probe 100 or any probe described above. Referring to probe 1400 of FIG. 15, the translational movement is created along a path that is substantially parallel to a guiding slot member 1471 located on a top supporting member 1470.

Figure 13:
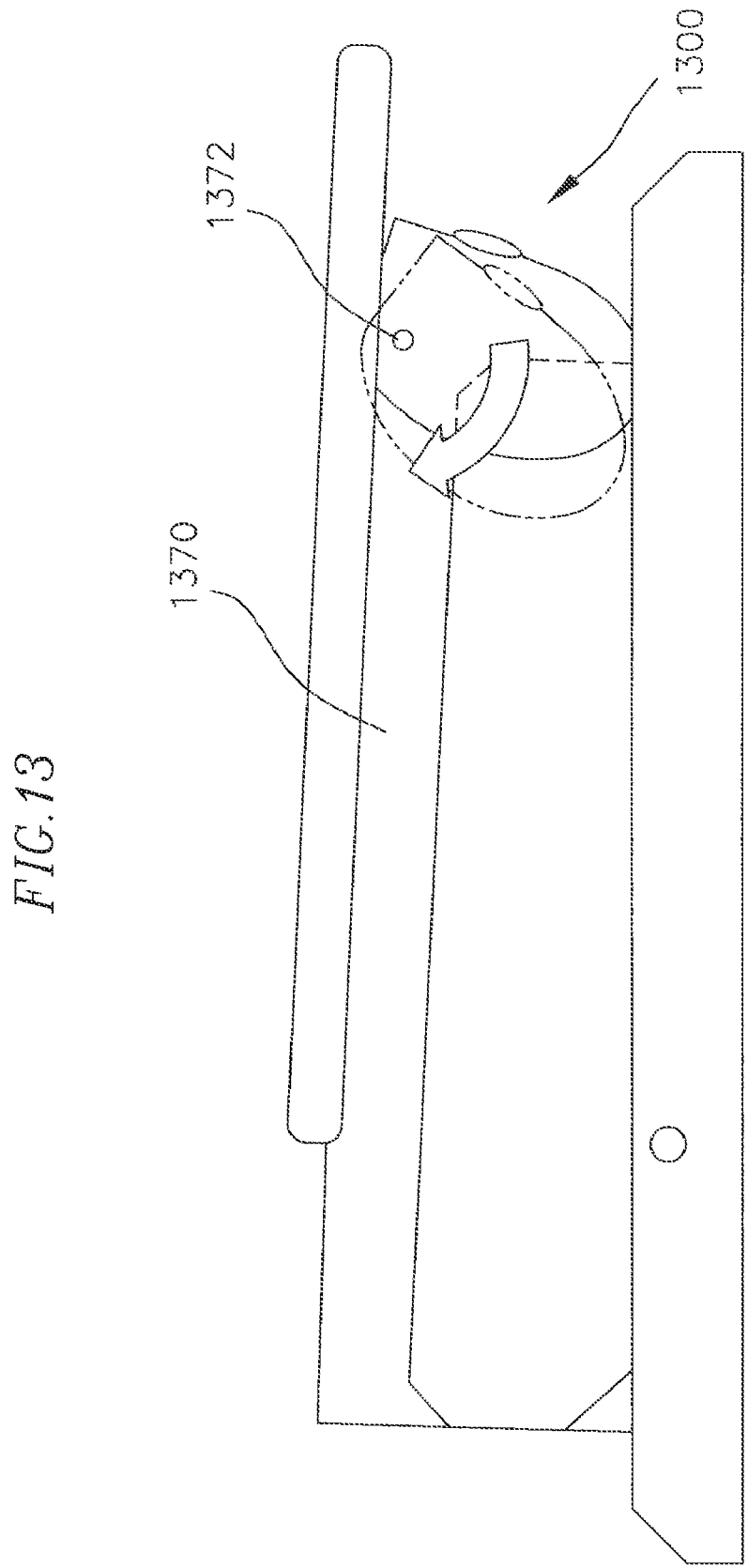
FIG. 13 illustrates a side view that depicts a rotational movement of a probe according to an embodiment of the present invention.
Figure 16:
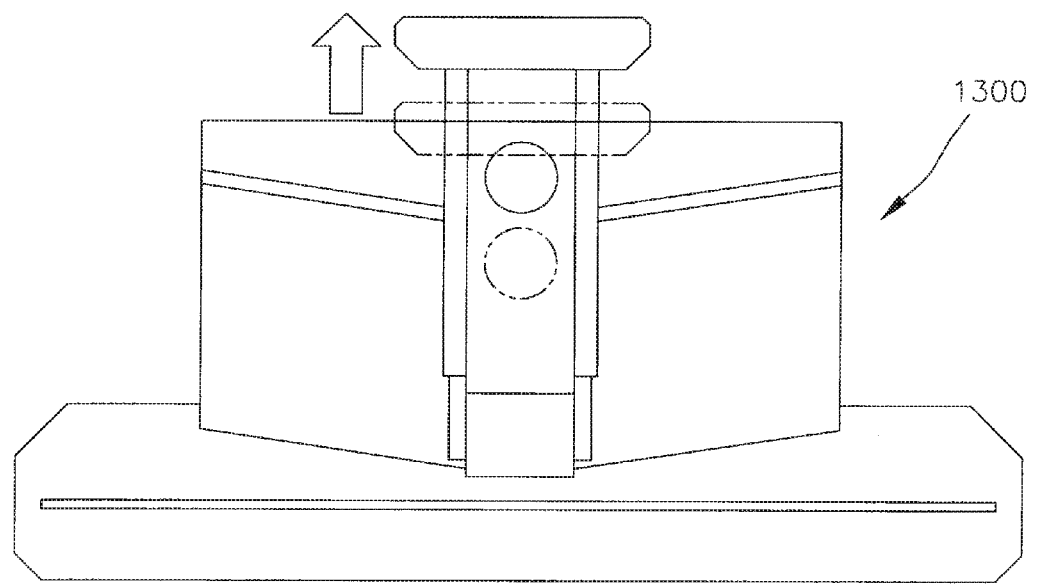
FIG. 16 illustrates a front view depicting a vertical movement of a probe according to an embodiment of the present invention.

FIG. 13 illustrates a rotational movement of a probe 1300 according to one embodiment of the present invention. Probe 1300 may exhibit some or all of the features of probe 100 or any probe described above. A front view of probe 1300 is shown in FIG. 16. Referring to FIG. 13, the rotational movement is created about a probe pin 1372. Similar to FIG. 15, the mechanism for creating rotational movement is also located on or near the top front of a supporting member 1370, which can be configured to accommodate a guiding slot to receive probe pin 1372 for translational movement as well.

According to an aspect of an embodiment of the present invention, as the probe is pressed against a subject's interstitial region, pressure is exerted to the probe causing it to slide along the guiding slot from an initial testing point to a final testing point. At the same time, the probe pivots about probe pin 1372 causing it to rotate from an initial contacting position to a final contacting position, where the probe is flush against the subject's interstitial region.

FIGS. 14 and 15 illustrate probe 1400 having both translational and rotational movements occur at or near the top supporting member 1470 according to another aspect of an embodiment of the present invention. Similar to probe 1300, probe 1400 may exhibit some or all of the features of probe 100 or any probe described above. As illustrated, probe 1400 rotates about a pivot point 1472 and slides back on a translational guide 1471, as the probe head is exerted against the subject's interstitial region.

In one embodiment, probe head 1400 is configured to have both rotational and translational movements. Rotational movement of probe head 1400 allows it to conform to the contours of the subject's testing area by varying the angle of the probe head 1400 with respect to the subject's testing area. Translational movement allows the probe to impart a consistent pressure on the subject's tissue.

FIGS. 16-18 illustrate probes 1200 and 1400 having a vertical movement according to some aspects of embodiments of the present invention. Probes 1200 and 1400 may exhibit some or all of the features of probe 100 or any probe described above. As shown in FIGS. 16-18, the vertical movement is a movement that is generally in an up and down direction along a path that is orthogonal (or substantially orthogonal) to the translational path.

According to aspects of embodiments of the present invention, each probe is attached to the second support by a second biasing member and a second probe pin. At a non-engaged stage, the probe is biased by the second biasing member with a substantially constant force toward a closed position.

As shown in FIGS. 17A and 18A, the vertical movement is created by having a second mounting support. In one embodiment the second substantially constant force is provided by a second biasing element 1782 and a second probe pin 1781, located at the distal end of the probe and at a bottom supporting structure 1780. In an embodiment, the second biasing element is an axial spring.

As depicted in FIGS. 17A and 17B, the vertical movement occurs when the top supporting member 1770 is lifted up by an insertion of a testing object that is to be measured spectroscopically. As the top supporting member 1770 is lifted up from a closed position (FIG. 17A), the whole unit pivots about the second probe pin 1781 and pushes down onto the second biasing element 1782 leaving a larger gap at the front in an open position (FIG. 17B). This vertical movement is important, for example, to accommodate different sizes or thicknesses of the testing object, such as the subject's fingers or hands. In an exemplary embodiment, the top supporting member is configured so that it is positioned to interact with the top of the subject's hand when the subject's fingers are placed into the housing. This allows the probe head to be repeatedly positioned at the appropriate height in a subject's interstitial area for optimal reflectance readings.

The height of the probe may also be driven automatically either with or without the presence of a top supporting member. A movable piston (not shown) may be incorporated into the apparatus that acts against biasing element 1782 to set the height of the probe for measurement. If a top supporting member is present, it may include a position sensor, such as a laser level, that detects the top of a user's hand or foot and position the probe accordingly. The top supporting member might also include a touch or pressure sensor and be brought down toward the top of a user's hand until the hand is contacted or until a preset pressure is reached. Settings may also be saved by the system such that once a user enters a code or is identified by the system, the probe moves to a particular height appropriate for that user.

FIGS. 18A and 18B illustrate a different mechanism for creating a vertical movement to accommodate a subject's body part while ensuring repeatable and accurate results by also providing translational and rotational movements.

According to FIGS. 18A and 18B, the second substantially constant force is provided by a second biasing element 1872 and a second probe pin 1873, where both the second biasing element 1872 and second probe pin 1873 are positioned at the top supporting structure 1870. In this embodiment, the second biasing element 1872 is an axial spring.

As can be seen in FIGS. 18A and 18B, the vertical movement occurs when the top supporting member 1870 is lifted up by an insertion of the testing object that is to be measured spectroscopically. As the top supporting member 1870 is lifted up from a closed position, it exerts pressure and compresses the second biasing element 1872 and pivots about the second probe pin 1873 leaving a larger gap at the front in an open position.

FIGS. 18A and 18B also depict the translational and rotational movements that are possible. FIG. 11 shows a top view of a similar mechanism illustrating the translational movement. In FIG. 11, the top supporting structure has been left off to show more clearly the operation of the probe head.

Probe Head

According to an aspect of the present invention, a probe device 100 or any other probe device described may include a probe head 40, source of electromagnetic radiation, such as fiberoptic bundle 50, and a detector. Probe head 40 may have an optical window made of a robust scratchproof material, such as optical grade sapphire. The optical window may serve as uniform measurement surface and protective layer for fiberoptic bundle 50. The optical window may be of a certain thickness to provide the least optical interference and adequate structural integrity to perform as a shielding mechanism for the probe head. In one embodiment, the optical window is mounted flush to the probe head 40 so that it can be adapted to conform to an interstitial location between fingers or toes of the subject.

Although the source of electromagnetic radiation is shown in the present embodiments as being a fiberoptic bundle, it should be understood that other sources are possible. For example, the initial source of the radiation could itself be positioned in the probe so that it does not have to be conveyed to the probe. Alternatively, radiation could be conveyed from a remote source to the probe by means other than fiberoptics. Non-imaging concentrators could be used for this purpose.

Figure 19A:
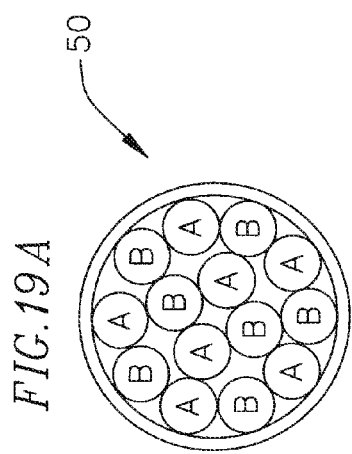
FIGS. 19A and 19B schematically show a cutaway view of a probe head with multiple source fiberoptics A and detector fiberoptics B, and a side view of a fiberoptic member that includes a fiberoptic strand and a detector fiberoptic strand according to an embodiment of the present invention.

FIG. 19A illustrates a fiberoptic bundle 50 according to an embodiment of the present invention. Referring to FIG. 19A, fiberoptic bundle 50 having at least one source fiberoptic strand (reference A) for conveying electromagnetic radiation from the electromagnetic radiation source to the probe head, and at least one detector fiberoptic strand (reference B), for receiving electromagnetic radiation reflected from the subject to the detector.

According to an aspect of an embodiment of the present invention, fiberoptic bundle 50 includes a plurality of source fiberoptic strands and a plurality of detector fiberoptic strands. Arrangements of the source and detector fiberoptic strands can be presented in various forms. It should be understood that in each of the arrangements depicted herein, the source and the detector fibers can be arranged so as to take each others place. In one embodiment, the source and detector fiberoptic strands are randomly dispersed with spacing distances between them at a constant gap or a predetermined distance.

Figure 19B:
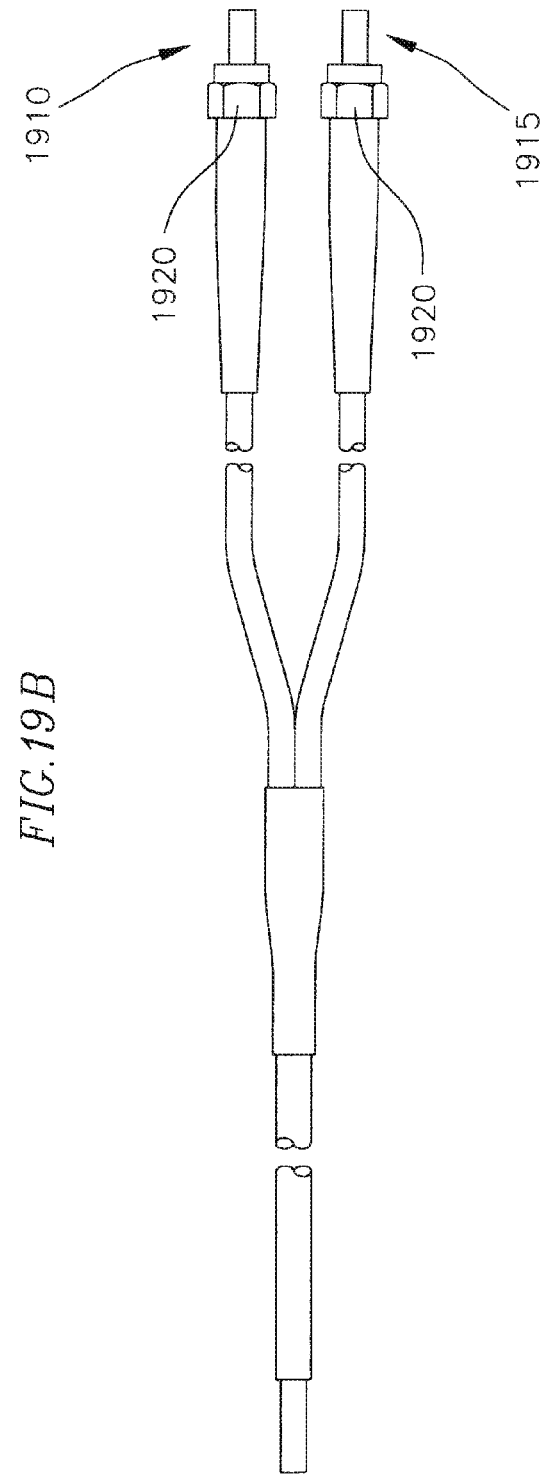

FIG. 19B shows schematic side view of a fiberoptic member that includes a bifurcated fiberoptic unit according to an embodiment of the present invention. In this embodiment, the bifurcated fiberoptic unit has one source fiberoptic strand 1910 and one detector fiberoptic strand 1915. Each individual strand can be protected with a plastic cover made of thermoplastic polymer, for example. Near a distal end of the unit, the strands are coupled together by fasteners or shrink-wrap plastics. Near a proximal end of the unit, the two strands of fibers are separated. Each strand is then encased in a protective layer and secured with a connector, such as an SMA connector 1920. By employing multiple bifurcated fiberoptic units, various arrangements of source fiberoptic strands and detector fiberoptic strands can be arranged, including in a randomized fashion.

According to another aspect of the invention, the source fiberoptics 1910 and detector fiberoptics 1915 can be arranged in an organized fashion and the spacing distances between them can be based on a range of constants or they can also be randomized.

In one embodiment, the fiberoptic bundle includes a plurality of detector fiberoptic strands where at least some of detector fiberoptic strands are arranged in a double row along an outer periphery of a plurality of source fiberoptic strands. FIG. 20 illustrates a fiberoptic bundle 2000 according to an embodiment of the present invention. Referring to FIG. 20, bundle 2000 has multiple layers or rows of source fiberoptics 2010 and detector fiberoptics 2020, where the source and detector fiberoptics are separated by rings of spacers 2100. In one embodiment, fiberoptic bundle 2000 is about 0.134 inches in diameter (OD) and spacer ring 2100 has a thickness of about 50 micrometers. In this way, the scattering effect of electromagnetic transmission can be eliminated or substantially reduced. The spacing also provides an optimal depth distance to detect certain desired attributes, such as measurement of blood components inside blood vessels near the skin surface.

According to another aspect of an embodiment of the present invention, the apparatus for non-invasive spectroscopic measurement also includes a depth measurement function. That is, to detect and account for the subject's tissues at varying depths.

Controlling the depth of the tissue examination may improve the reproducibility, accuracy, or precision of the blood alcohol measurements obtained from the subject. Variation of the target depth of the spectroscopic measurement allows the device to account for differences in the thickness of a subject's skin and adipose tissue, and to optimize the quality of the signal acquired. Placement of the detector fiberoptics relative to the source fiberoptics may be varied to tune the depth to which the subject's tissue is probed. In addition, the density of the detector fiberoptics may be varied to tune the depth to which the subject's tissue is measured.

Depth variation of the spectroscopic measurement may be achieved by any suitable means, for example, the use the spatial arrangement of the detector fiberoptics, with respect to the source fiberoptics, to selectively emphasize the collection of electromagnetic radiation of a particular path length or path lengths. By selectively emphasizing the path length of the electromagnetic radiation collected, the present invention can control the depth to which the subject's tissue is spectroscopically measured. Locating the detector fiberoptics in close proximity to the source fiberoptics may selectively emphasize electromagnetic radiation of shorter path length, and may be suitable for subjects whose tissue does not require significant measurement depth. Placement of the detector fiberoptics further away from the source fiberoptics may emphasize electromagnetic radiation of longer path length, and may be suitable for subjects whose tissue requires greater depth of spectroscopic measurement.

As the distance between the source fiberoptics and the detector fiberoptics increases, the space available for incorporating detector fiberoptics may also increase. Consequently, the detector fiberoptics placed at greater distances from the source fiberoptics may be present in greater numbers than the detector fiberoptics that are positioned closer to the source fiberoptics. Thus, if the density of detector fiberoptics does not change as the distance from the source fiberoptics changes, the signal received may be weighted with the signal from the detector fiberoptic bundles farthest from the source fiberoptic bundle. However, as the path length of the electromagnetic radiation increases, its magnitude may also decrease. As a result, greater numbers of detector fiberoptic bundles at larger distances from the central source fiberoptics may be required to emphasize electromagnetic radiation of longer path lengths. FIGS. 21-25 illustrate a few examples of such configurations, in rectangular, elliptical, and radial manners that have varied density of the detector fiberoptics as the distance between the detector fiberoptics and the source fiberoptics changes.

In one embodiment, detector fiberoptics are arranged in a ring or in a radial manner away from a plurality of source fiberoptics. The detector fiberoptics of each ring can operate and detect electromagnetic radiation independently from other detector fiberoptics in other rings. Further, within each ring there may be smaller independent regions where the detector fiberoptics in one region may operate independently from detector fiberoptics in other regions.

In one embodiment, to enhance clear spectroscopic measurements, the source fiberoptics and the closest detector fiberoptics may be separated by a partition that will be of a material that will not contribute to signal degradation. Detection of electromagnetic radiation may then be accomplished by selectively engaging each detector fiberoptic, each region of each ring, or each ring independently or in combination until the desired signal is obtained from the subject. Detector fiberoptics that do not contribute to the acquired spectra in a desired way may be deactivated, or the signal received from those detectors may be discarded. Alternatively, the device may engage all detector fiberoptics simultaneously, retain and average the signal obtained from every detector, resulting in spectra that represent an average of many different path lengths.

The detector fiberoptics may be spatially arranged around the source fiberoptics in a variety of ways. In one embodiment, the detector fiberoptics may radiate out from the source fiberoptics in a straight line. Alternatively, the detector fiberoptics may radiate from the central source fiberoptics in a zigzag pattern. In another embodiment, the detector fiberoptics may radiate out from the source fiberoptics in a semicircular or elliptical manner that results in spirals of detector fiberoptics. The detector fiberoptics may also be spatially arranged around the source fiberoptics in a randomized fashion. Similarly, the source fiberoptics may be randomly distributed among the detector fiberoptics. Spatial arrangement of the detector fiberoptics relative to the source fiberoptics may be accomplished by any suitable means that achieves a desired signal.

Figure 21:
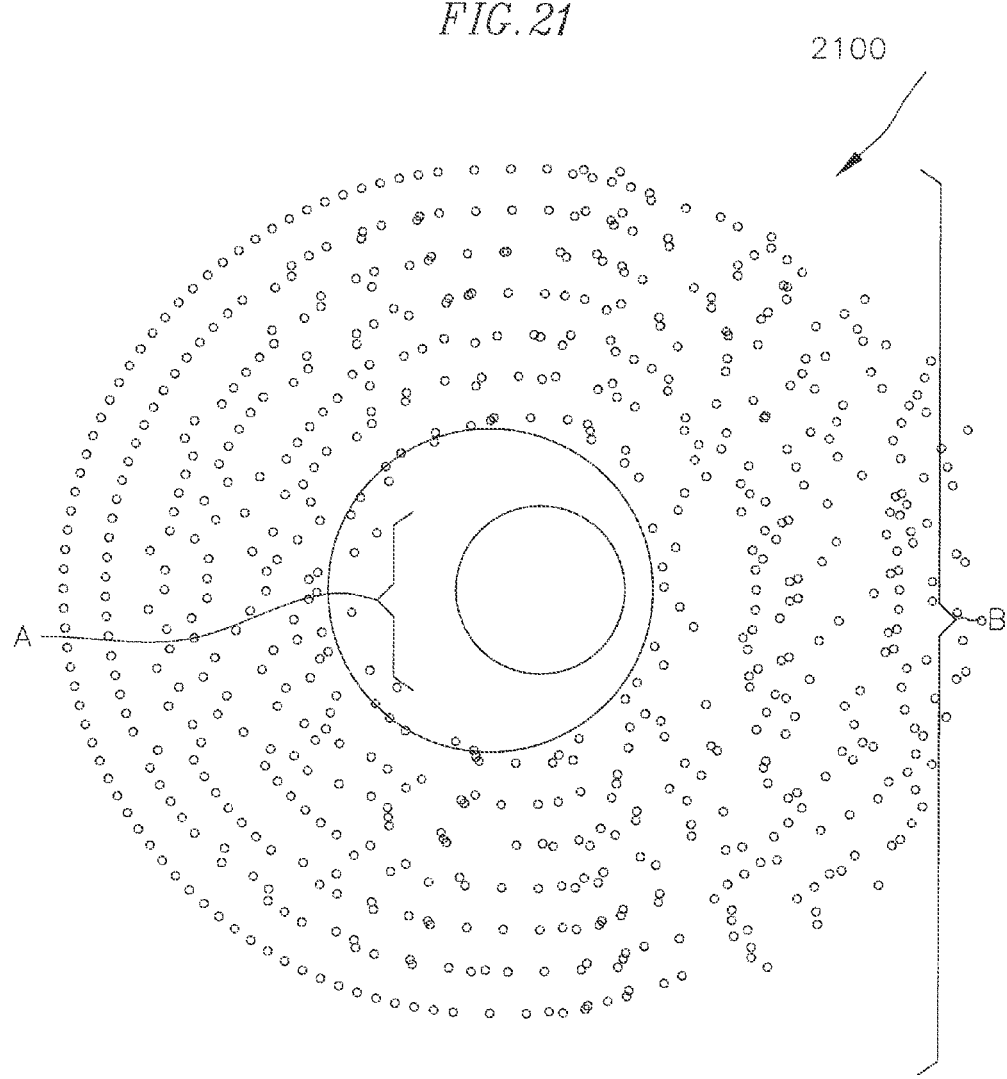
FIG. 21 illustrates a cutaway view of a probe head having a plurality of source fiberoptics surrounded by a plurality of detector fiberoptics according to another aspect of an embodiment of the present invention.
Figure 22:
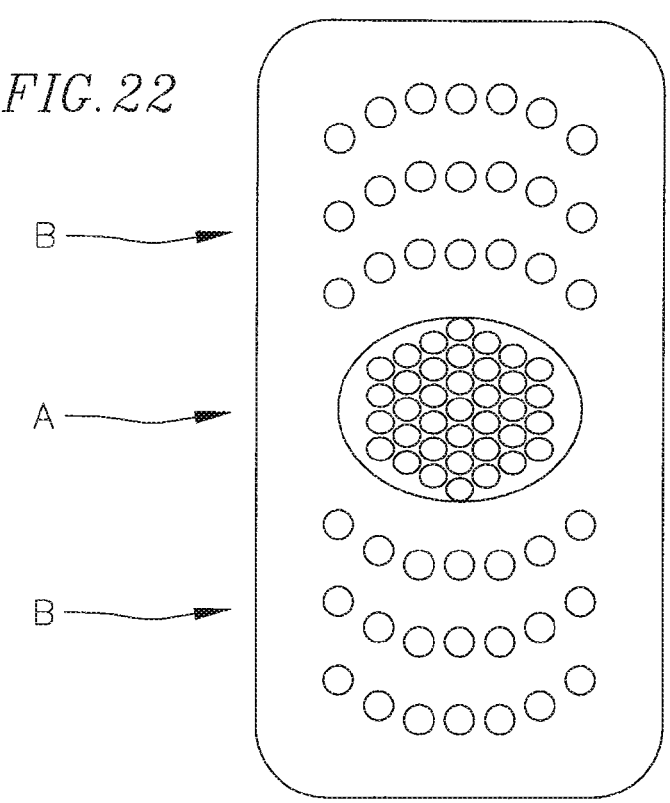
FIG. 22 illustrates a cutaway view of a probe head having a plurality of source fiberoptics surrounded by a plurality of detector fiberoptics arranged in ellipsoid arcs on two sides of the source fiberoptics according to another aspect of an embodiment of the present invention.
Figure 23:
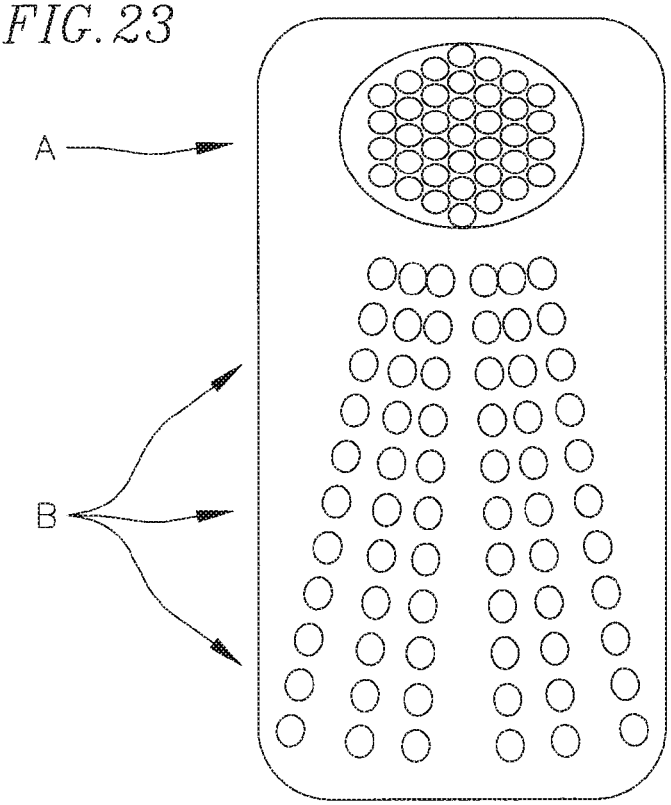
FIG. 23 illustrates a cutaway view of a probe head having a plurality of detector fiberoptics located on one side and a plurality of source fiberoptics located on the other side according to an aspect of an embodiment of the present invention.
Figure 24:
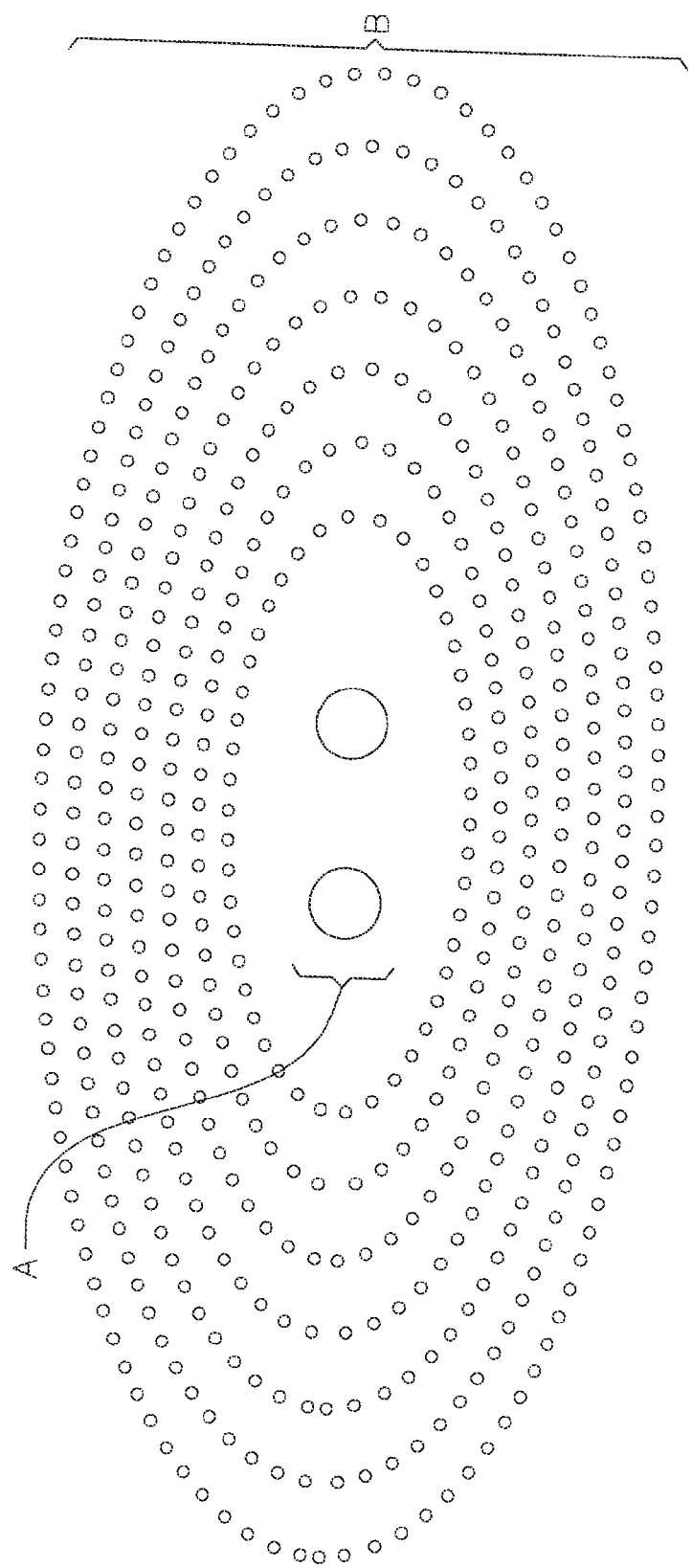
FIG. 24 illustrates another cutaway view of a probe head that includes a plurality of source fiberoptic bundles and a plurality of detector fiberoptics according to another aspect of an embodiment of the present invention.
Figure 25:
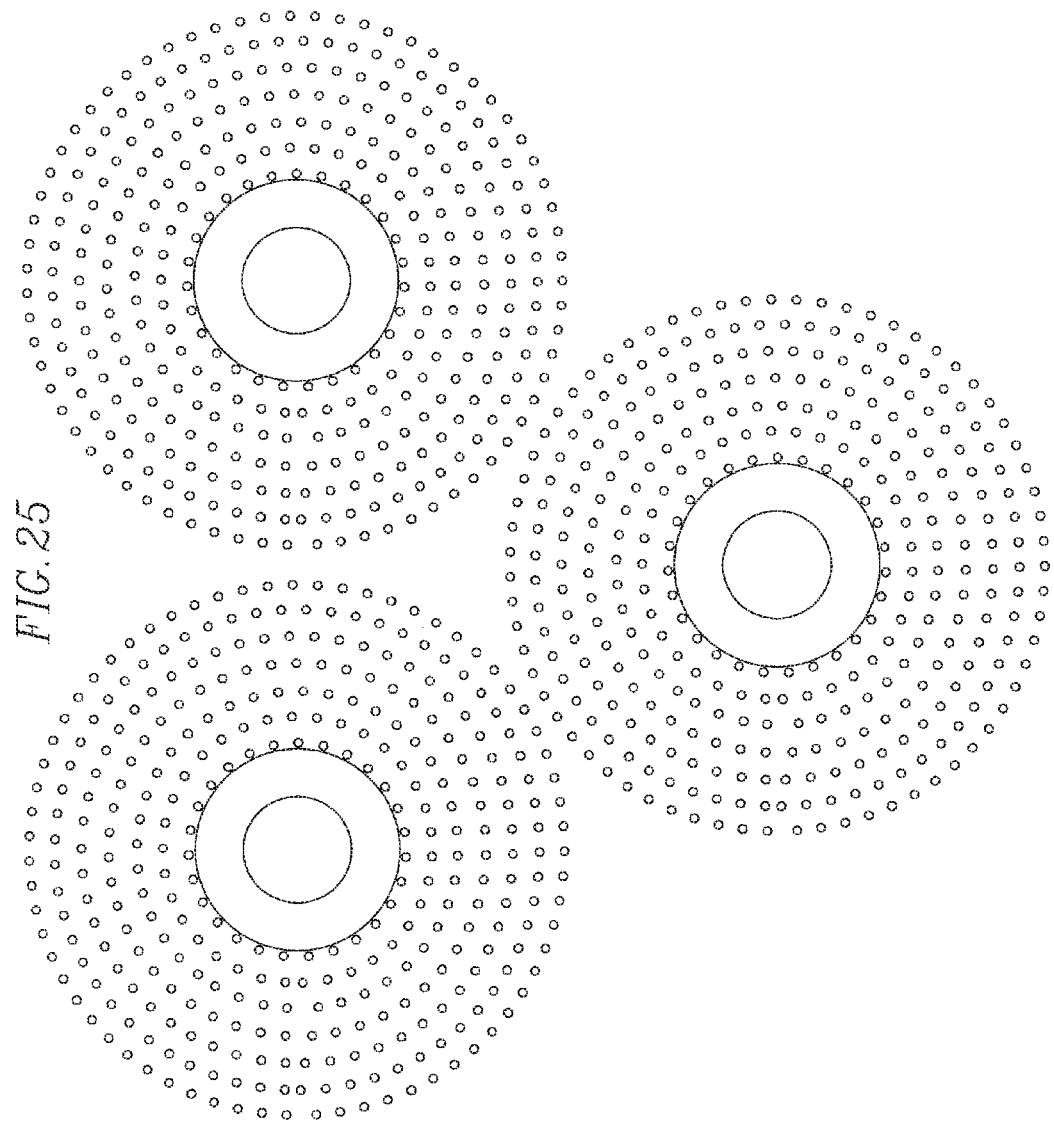
FIG. 25 illustrates an overhead view of a probe head with multiple source fiberoptics, each surrounded by concentric rings of detector fiberoptics according to another aspect of an embodiment of the present invention.

FIG. 21 illustrates a fiberoptic bundle 2100 according to an embodiment of the present invention. Referring to FIG. 21, fiberoptic bundle 2100 includes source fiberoptics A surrounded by an array of rings of detector fiberoptics B. The distance between each ring of detector fiberoptics may be fixed or varied. In addition, the distance between the fiberoptics within each ring may be a fixed, or may be varied from ring to ring, or within each ring.

According to another aspect of an embodiment of the present invention, the apparatus for non-invasive spectroscopic measurement includes a temperature detection mechanism. In one embodiment, the temperature detection mechanism resides within the housing of the apparatus. The temperature detection mechanism can be infrared, thermocouple, or any others that can be used to measure a subject's local temperature at the site of the spectroscopic measurement, the subject's core or mean body temperature, ambient temperature at or near the site of the spectroscopic measurement, or the temperature of the probe at or near the site of the spectroscopic measurement.

The core body temperature or local body temperature of the subject may have an effect on the accuracy, precision, or reproducibility of the measurements acquired from the subject. These temperature effects may be traced to variation in the subject's blood flow, changes in the chemical composition or hydration level of the subject's blood stream or surrounding tissue, or to other physical manifestations of temperature change, such as changes in the subject's tissue density or depth. The collected temperature data is useful for correlation with the obtained spectroscopic measurements, for example, and/or with other data for proper interpretations of the result. The temperature data may be collected before, after, or concurrently with the spectroscopic data measurement.

In one embodiment, the temperature data may be collected by an infrared probe using the same source fiberoptics and detector fiberoptics as used for the spectroscopic measurement.

Alternatively, the fiberoptics used for the infrared temperature measurement may be distinct from the fiberoptics used for the spectroscopic measurement. In one embodiment, a separate fiberoptic bundle dedicated to the infrared temperature measurement may be housed within the probe head used for the spectroscopic measurement. In that embodiment, the subject's temperature may be measured at, or very close to, the site of the spectroscopic measurement.

In another embodiment, the separate fiberoptic bundle dedicated to the infrared temperature measurement may be housed separately from the probe head. The separate fiberoptics may be used to measure the temperature of the subject's skin in an area near the region to spectroscopically measured, such as the subject's hand, wrist, foot, or ankle. Alternatively, the separate fiberoptic bundles may be used to measure the temperature of the subject's skin in an area further from the region to be spectroscopically measured, such as the subject's forearm or lower leg.

In yet another embodiment, the temperature measurement may be made by a thermocouple placed within the spectroscopic probe head. The thermocouple may be positioned such that it contacts the subject's skin and measures temperature data before, during, or after the spectroscopic measurement. Alternatively, the thermocouple may be positioned within the probe head such that it is adjacent to the subject's skin and measures ambient or probe head temperature data before, during, or after the spectroscopic measurement.

In another embodiment, the thermocouple for measuring the subject's temperature at or near the region to be spectroscopically measured may be housed outside the probe head. The thermocouple may also be positioned so as to measure the temperature of the subject's skin further from the region to be spectroscopically measured, such as the subject's forearm, upper arm, lower leg, upper leg, torso, head, or neck. Other means for measuring the subject's temperature may be suitable, including analog, digital or spectroscopic means.

In an embodiment of the present invention, the temperature data is used in the application of a corrective algorithm to the spectroscopic data or to the apparatus itself. The spectroscopic data may be processed using the corrective algorithm in such a way that accounts for variations in temperature. The corrective algorithm may be applied during or after the acquisition of the spectroscopic data. The corrective algorithm may be applied one or more times, and the number of applications of the algorithm may vary with temperature.

Alternatively, the temperature data collected may be used to alter the spectroscopic device itself. In one embodiment, the present invention may use temperature data to change the manner in which the spectroscopic data is collected. Based on temperature data, the instrument may change the range of frequencies examined, the intensity of the incident electromagnetic radiation, or the pressure applied by the probe head. Alteration of the present invention's method of data collection to account for changes in temperature may be made by any suitable method.

In an embodiment of the present invention, the apparatus acquires both spectral information from a subject along with the subject's biometric information. The resulting spectra are converted to information regarding the chemical components, such as alcohol or its metabolic byproduct concentrations, present in the subject's blood by way of multivariate calibration techniques (e.g. principal component analysis or partial least squares), and the biometric verification is used to confirm the subject's identity.

In one embodiment, the biometric verification system can be accomplished by way of a fingerprint or toe print scan. The system could prevent operation of a vehicle if the presence of alcohol or other prohibited substance is detected in the subject. Similarly, the system can prevent operation of the vehicle if the subject's biometric authentication does not indicate an authorized user. Results of the biometric scan and spectroscopic measurement would be stored in the system for a selected number of users, and for a selected period of time.

According to an aspect of an embodiment of the present invention, the spectroscopic analysis of the subject is performed at the interstitial region between a subject's fingers or toes, or the interstitial region adjacent to a single finger or toe. The interstitial regions between any two fingers or toes of the subject may also be used. In one embodiment the interstitial region between the subject's index and middle fingers are analyzed. The housing may be large enough to accommodate a subject's single finger, two fingers, multiple fingers, or entire hand. The housing may also accommodate a subject's single toe, two toes, multiple toes, or entire foot.

Figure 26:
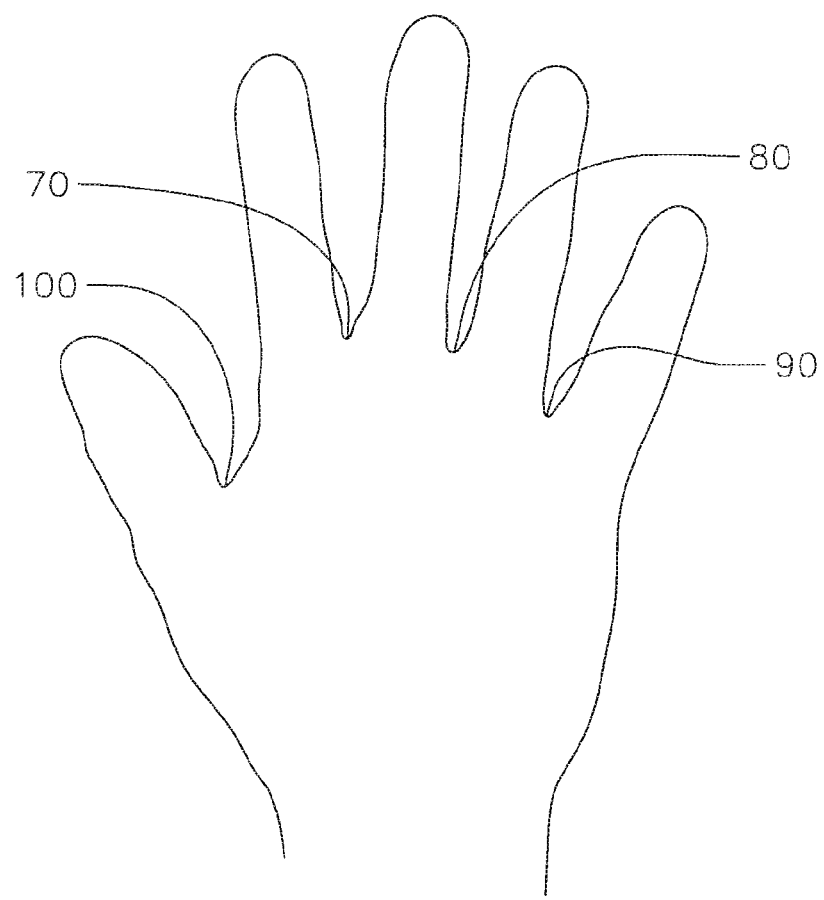
FIG. 26 illustrates a subject's hand with interstitial regions between the fingers at which spectroscopic measurements can be taken according to one aspect of an embodiment of the present invention.

FIG. 26 shows a subject's tissue in the interstitial regions 70, 80, 90, or 100 between the subject's fingers that can used for spectroscopic measurements according to an embodiment of the present invention. Preferably the region targeted is that between the base of a subject's fingers and between the plane of the subject's palm and the top of the subject's knuckles. Any location in this general region able to absorb and reflect the incident radiation should be suitable. Advantages of measuring in the interstitial regions include low interference with the readings because the interstitial regions have relatively low density of muscle bodies, particularly in the regions between the palmar interossei and dorsal interossei muscles. Muscle bodies can contain significant variations in the concentration of lactic acid, which may interfere with the reliable detection of alcohol. Spectroscopic measurements taken in regions with higher muscle body densities, such as the forearm, can be influenced by the presence of lactic acid, and consequently may produce less reliable results in the detection of alcohol. The interstitial region between a subject's fingers is minimally affected by the presence of lactic acid in the muscles. Accordingly, measurements at the interstitial regions 70, 80, 90, or 100 between the subject's fingers are preferred.

Figure 27:
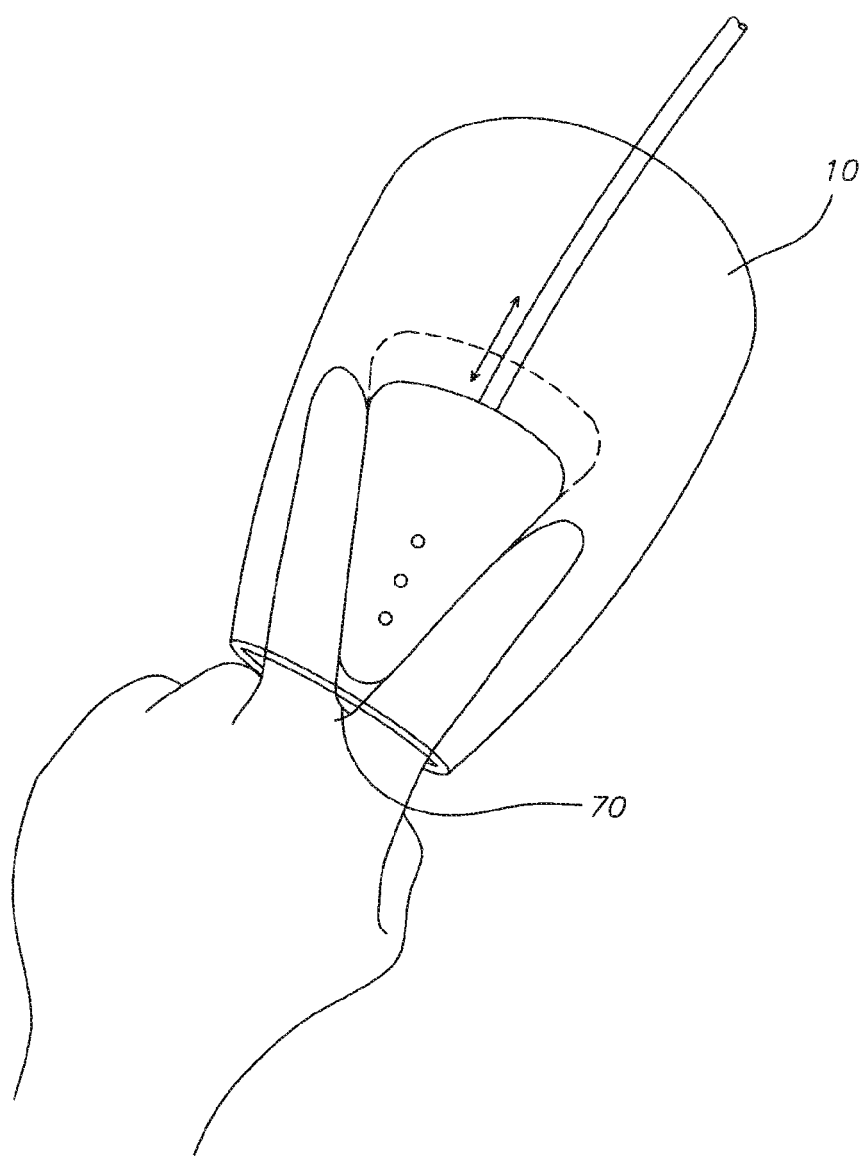
FIG. 27 illustrates a cutaway pictorial view of a two-finger apparatus with a subject's fingers entering the housing of the apparatus according to one aspect of an embodiment of the present invention.

FIG. 27 illustrates an exemplary embodiment of the present invention, where a subject's interstitial region 70 being inserted into the apparatus housing 10 allowing the probe head to slide between the fingers and seat flushed against the interstitial region 70 between the subject's fingers to obtain a spectroscopic reading.

Another aspect of an embodiment of the present invention is directed toward a use of a single finger, toe, or digit of a subject in a simple way to simultaneously activate the apparatus for identifying the subject, scanning, and determining the blood alcohol content of the subject, and conclude the scanning.

FIG. 28 shows various embodiments of the present invention where various parts of the apparatus are designed to assert a constant pressure when applied to a subject and/or adapted to be received at an interstitial location between fingers or toes of the subject.

In one embodiment, the probe has a pie configuration, where the probe body is stationary mounted on the housing and the probe bead is biased by a substantial constant force exerted by a biasing element toward an initial testing point. In this embodiment, as the subject's interstitial region is pressed against the probe head, the probe head is pushed back along a path that is parallel (or substantially parallel) to the probe body.

In another embodiment, both the probe head and probe body are biased toward the initial testing point, where the probe body is biased by a second substantial constant force exerted by a second biasing element.

Figure 29:
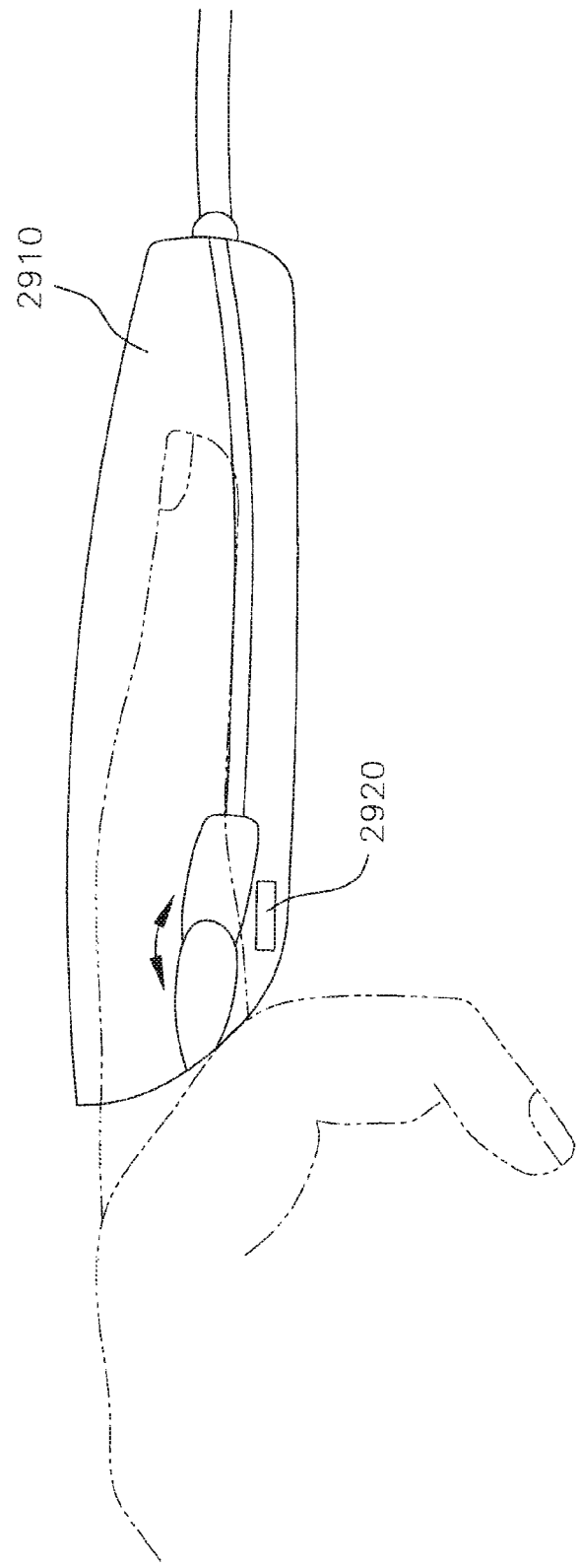
FIG. 29 illustrates a side view of a one-finger apparatus with a subject's finger entering the housing of the apparatus according to an embodiment of the present invention.

FIG. 29 shows an embodiment of the present invention where a single finger is inserted into the housing 2910 of the apparatus. Housing 2910 may exhibit some or all of the features of housing 10 or any housing described above. In one embodiment, housing 2910 also includes a biometric verification system 2920. As the finger enters housing 2910 of the apparatus, the probe presses the interstitial region between the index finger and ring finger to obtain a spectroscopic reading. The finger may be guided by an ergonomically designed motion guide to direct the finger into the device in an optimal measurement position.

Before, during or at the conclusion of the scan, the user or subject may be given a signal by visual, audio, tactile, physical, electronic, or other means to communicate the readiness for scan, results of the scan, when it is time for the subject to be scanned again, or other information that is relevant to the subject's use of the apparatus.

Figure 30:
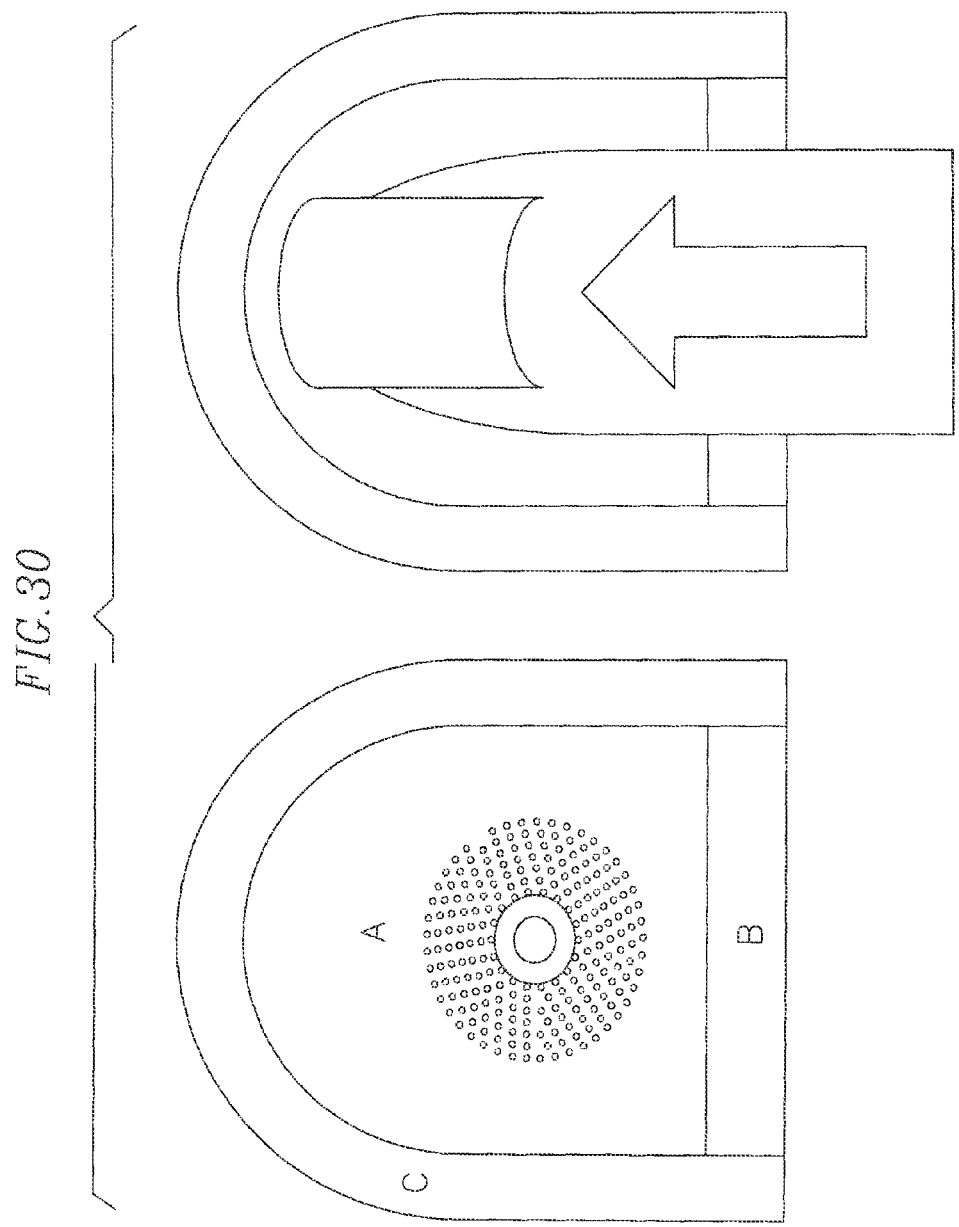
FIG. 30 illustrates a series of top down views of a human interface apparatus, having an optical device window A, biometric device B, and an ergonomic finger motion guide C according to an embodiment of the present invention.
Figure 31:
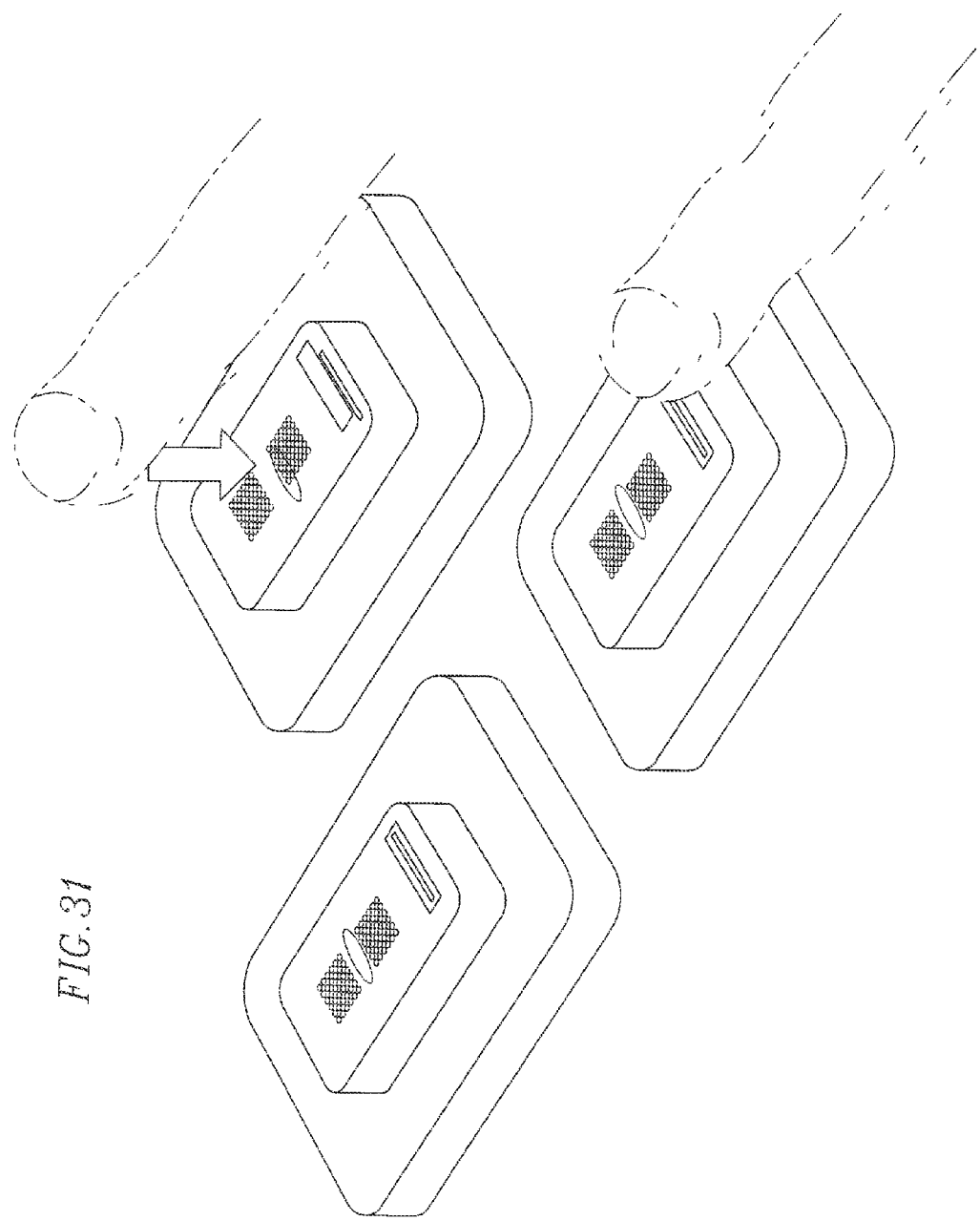
FIG. 31 illustrates multiple pictorial views of an apparatus for non-invasive spectroscopic measurement that includes detector fiberoptics arranged about a central source fiberoptic bundle in straight-line rows parallel to the source fiberoptic bundle, and its use according to one aspect of an embodiment of the present invention.
Figure 32:
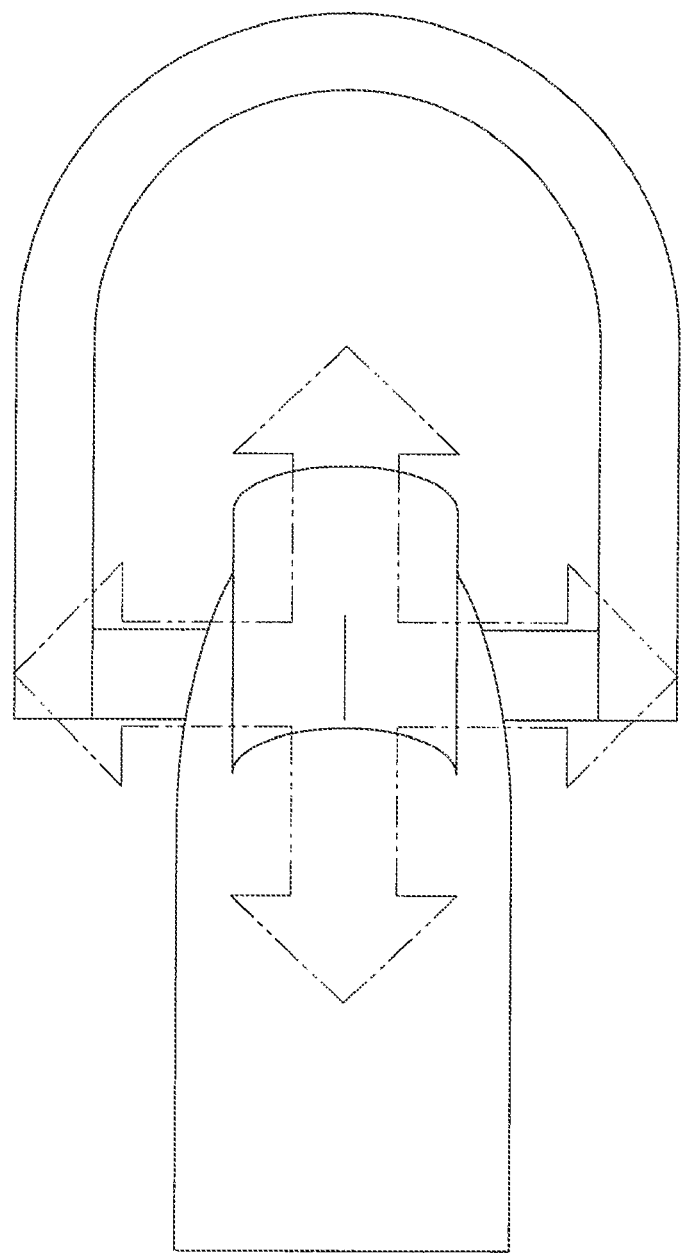
FIG. 32 illustrates a top view of a user interface for data input by way of pressure, motion, or directional input according to another aspect of an embodiment of the present invention.

Other aspects of embodiments of the invention are directed toward a use of a pad, button, or knob of the spectroscopic probe as data input interfaces. FIGS. 30-32 illustrate certain aspects of embodiments of the present invention, where the spectroscopic reading is obtained from the tip of a finger. The subject can either make contact with the probe either by pressing on the pad or sliding the tip of the finger into place.

Another aspect of an embodiment of the present invention is directed toward controlling the data input by the subject by way of pressure, directional motion relative to the device; or in the instance of the knob, by movement of the device itself. Directional motion relative to the device may include movement in the horizontal and vertical planes (see FIG. 31 and FIG. 32). Input from the subject may be used to turn the device on, access software, make selections, navigate through software menus, confirm system actions, request system actions, or activate any other software related purpose that requires input from the subject.

Another aspect of an embodiment of the present invention is directed toward a finger print sensor. The fingerprint sensor may interpret the subject's motions as actions for initiating certain sequences for hardware and/or the software controls. For example, pressing or tapping the pad, button, or knob may function as select or confirm actions in the software. Swiping motions along the device may serve to scroll through software menus. The software in the present invention may respond to user inputs in a sensory fashion including but not limited to: visual or graphical, audio, tactile, physical, or electronic. The various user inputs may be used independently or in any combination.

Another aspect of certain embodiments of the invention is to account for multiple variables present in the obtained spectra by comparison to reference signals contained within the spectra. For example, the signal attributed to water may be used to account for the subject's skin hydration level and blood volume in the region being spectroscopically measured. Other factors, such as the subject's whole body hydration level, blood flow, temperature, heart rate, diet, and other physiological conditions may be accounted for by referencing the signal attributed to water. In another example, signals that relate to the nature or quantity of keratin or collagen of the dermis, or the fatty layer of the hypodermis may be used in processing the acquired spectra. Signal referencing may also be useful to account for variations in other blood components, such as blood cells, urea, creatinine, glucose, oxygen, or chemicals ingested by the subject.

Additionally, the present invention may account for non-physiological skin components. Such components may adversely impact the quality of the spectroscopic data obtained from the subject. For example, the presence of tattoo ink in the dermis layer of the subject's skin may be identified by the device and a spectral library of common tattoo ink may be factored into the data analysis if spectra are collected from a tattooed user. The spectral library may also include attenuation factors to account for the depth of the tattoo ink in the subject's dermal layer. In addition, if the device identifies the presence of tattoo ink, the device may modify the detector bundle selection criteria to optimize the signal that can be obtained from a tattooed subject.

What is claimed is:

1. A method for non-invasively evaluating bodily fluids of a subject, comprising:

providing a source of electromagnetic radiation to a device;

supporting a lower surface of at least one of a pair of adjacent fingers of the subject;

using the device, guiding the adjacent fingers of the subject apart from one another; and positioning the device at an interstitial location between the fingers of the subject; and receiving the electromagnetic radiation reflected from the subject, wherein the interstitial location is that between the base of the subject's fingers and in a region between the plane of the subject's palm and the top of the subject's knuckles, and above the web.

2. The method of claim 1 also comprising applying the device to a surface of the subject at a substantially constant pressure.

3. The method of claim 2 wherein the device is applied so as to be substantially flush with the surface of the subject.

4. The method of claim 1 wherein the interstitial location is between first and second fingers of the subject.

5. The method of claim 1 wherein the electromagnetic radiation is near infrared radiation.

6. An apparatus for non-invasively evaluating bodily fluids of a subject, comprising:

means for providing a source of electromagnetic radiation to a device;

means for supporting a lower surface of at least one of a pair of adjacent fingers or toes of the subject;

means for guiding the adjacent fingers or toes of the subject apart from one another such that the device is positioned at an interstitial location between the fingers or toes of the subject not including the web; and means for receiving the electromagnetic radiation reflected from the subject.

7. The apparatus of claim 6 also comprising means for applying the device to a surface of the subject at a substantially constant pressure.

8. The apparatus of claim 7 also comprising means for applying the device so as to be substantially flush with the surface of the subject.

9. The apparatus of claim 6 wherein the interstitial location is between first and second fingers of the subject.

10. The apparatus of claim 6 wherein the electromagnetic radiation is near infrared radiation.

11. An apparatus for non-invasively evaluating bodily fluids of a subject, comprising:
- a mounting support for a probe that defines at least one path of translational movement along a surface of the mounting support;
- a probe comprising a probe head and a probe body, wherein the probe body having a proximal end and a distal end, and the probe head is pivotally attached to the probe body and adapted to move along a pivotal path relative to the mounting support; and
- a biasing element that exerts substantially constant force to provide translational movement of the probe;
- wherein the probe is translationally movable along the at least one path in a direction away from an initial point, and the probe is biased by the substantially constant force exerted by the biasing element toward the initial point.

12. The apparatus of claim 11 wherein the probe is also movable up and down along a second path that is substantially orthogonal to the at least one path.

13. The apparatus of claim 11 wherein the biasing element is a coil spring.

14. An apparatus for non-invasively evaluating bodily fluids of a subject, comprising:
- a base adapted to support a lower surface of at least one of a pair of adjacent fingers or toes of the subject;
- a probe movably positioned above the base;
- a biasing element exerting a substantially constant force on the probe toward an interstitial location not including the web between the adjacent fingers or toes of the subject while the apparatus is in use; and
- a guide member located above the base and adapted to guide the adjacent fingers or toes of the subject apart from one another and position the subject's interstitial location not including the web in front of the probe while the apparatus is in use.

15. The apparatus of claim 14 also comprising a biometric verification device located at the base and adapted to provide biometric verification of the subject from the lower surface of the at least one of a pair of adjacent fingers or toes of the subject.

16. The apparatus of claim 14 wherein the base is adapted to support the lower surface of both of a pair of adjacent fingers or toes of the subject.

17. The apparatus of claim 14 wherein the probe is movable both in a direction along the base relative to the interstitial location and pivotally relative to the base.

18. A probe for non-invasively evaluating bodily fluids of a subject, comprising:
- a base adapted to support a lower surface of at least one of a pair of adjacent fingers or toes of the subject;
- a source of electromagnetic radiation;
- a probe head;
- at least one fiberoptic for conveying electromagnetic radiation from the source to the probe head;
- a detector;
- at least a second fiberoptic for conveying electromagnetic radiation reflected from the subject to the detector; and
- a guide member located above the base and adapted to guide the adjacent fingers or toes of the subject apart from one another,
- wherein the probe head is adapted to be received at an interstitial location not including the web between the adjacent fingers or toes of the subject.

19. The probe of claim 18 wherein the probe is biased toward the interstitial location by a substantially constant force.

20. The probe of claim 18 wherein the probe head is pivotable so as to be able to pivot to be substantially flush with a surface of the subject.

21. The probe of claim 18 wherein the probe head is adjustable up and down relative to the interstitial location.

22. The probe of claim 18 wherein the source of electromagnetic radiation generates near infrared radiation.

* * * * *